(12) United States Patent
Tomlinson

(10) Patent No.: US 7,115,570 B2
(45) Date of Patent: Oct. 3, 2006

(54) CLONING AND CHARACTERIZATION OF A HUMAN ADENYLYL CYCLASE

(75) Inventor: James E. Tomlinson, Burlingame, CA (US)

(73) Assignee: Bayer Healthcare AG, Leverkusen (DE)

( * ) Notice: Subject to any disclaimer, the term of this patent is extended or adjusted under 35 U.S.C. 154(b) by 39 days.

(21) Appl. No.: 10/991,327

(22) Filed: Nov. 17, 2004

(65) Prior Publication Data

US 2005/0148051 A1 Jul. 7, 2005

Related U.S. Application Data

(60) Division of application No. 10/201,000, filed on Jul. 24, 2002, now Pat. No. 6,864,081, which is a division of application No. 09/474,076, filed on Dec. 29, 1999, now Pat. No. 6,465,237, which is a continuation of application No. PCT/US98/13694, filed on Jul. 1, 1998.

(60) Provisional application No. 60/070,904, filed on Jul. 1, 1997.

(51) Int. Cl.
*A61K 38/00* (2006.01)
*C07K 1/00* (2006.01)
*C12N 9/88* (2006.01)

(52) U.S. Cl. .......... 514/12; 530/350; 435/232

(58) Field of Classification Search ........ 530/350; 435/232; 514/12
See application file for complete search history.

(56) References Cited

U.S. PATENT DOCUMENTS 5,334,521 A  8/1994  Ishikawa
6,268,477 B1  7/2001  Gray et al.
6,752,987 B1*  6/2004  Hammond et al. ........ 424/93.2

FOREIGN PATENT DOCUMENTS

| EP | 543137 A1 | 6/1993 |
| WO | WO 95/30012 | 9/1995 |
| WO | WO 98/10085 | 12/1998 |
| WO | WO 99/01547 | 1/1999 |

OTHER PUBLICATIONS

Defer, et al., "A Molecular Cloning of the Human Type VIII Adenylyl Cyclase," *FEBS Letters*, 351:109-113, 1994.
Nomura, et al., "A Prediction of the Coding Sequences of Unidentified Human Genes. I. The coding Sequences of 40 New Genes (KIAA0001-KIAA0040) Deduced by Analysis of Randomly Sampled cDNA Clones from Human Immature Myeloid Cell Line KG-1," *DNA Research*, 1(1):27-35, 1994.
Stengel, et al., "A Different Chromosomal Localization of Two Adenylyl Cyclae Genes Expressed in Human Brain," *Hum. Genet.*, 90:126-130, 1992.
Haber, et al., A Chromosomal Mapping of Human Adenylyl Cyclase Genes Type III, Type V and Type VI, *Hum. Genet.*, 94(1):69-73, 1994.
Hellevuo, et al., "A Novel Adenylyl Cyclase Sequence Cloned from the Human Erythroleukemia Cell Line," *Biochem. Biophys. Res. Comm.*, 192(1):311-318, 1993.
Katsushika, et al., "A Cloning and Characterization of a Sixth Adenylyl Cyclase Isoform: Types V and VI Constitute a Subgroup within the Mammalian Adenylyl Cyclase Family," *Proc. Natl. Acad. Sci. USA*, 89(18):8774-8778, 1992.
Yoshimura, et al., "A Cloning and Expression of a $Ca^{2+}$-Inhibitable Adenylyl Cyclase from NCB-20 Cells," *Proc. Natl. Acad. Sci. USA*, 89(15):6716-6720, 1992.

\* cited by examiner

*Primary Examiner*—Maryam Monshipouri
(74) *Attorney, Agent, or Firm*—Banner & Witcoff, Ltd.

(57) ABSTRACT

A DNA sequence encoding a human adenylyl cyclase is described. The amino acid sequence of the adenylyl cyclase is also described.

6 Claims, 9 Drawing Sheets

FIG. 1A

```
GCGGACGGCG GACGGCGGAC GGCGGGCGGG ACGGCCAGGA CGCGCGGGCT    50
CGCCTGCCGC CTGCCGCCTG CCGCCCGCCC TGCCGGTCCT GCGCGCCCGA

CGGAGGACCG CGGGACGGCC GGCCGGCCGG CCGGAGCCCG CGGGGCGGC    100
GCCTCCTGGC GCCCTGCCGG CCGGCCGGCC GGCCTCGGGC GCCCCCGCCG

GGGGCGGGGG CCCAGGGCAG GCGCGGAGCC GGGCCGGCAG CAACATGTCA   150
CCCCGCCCCC GGGTCCCGTC CGCGCCTCGG CCCGGCCGTC GTTGTACAGT
                                              MetSer

TGGTTTAGTG GCCTCCTGGT CCCTAAAGTG GATGAACGGA AAACAGCCTG   200
ACCAAATCAC CGGAGGACCA GGGATTTCAC CTACTTGCCT TTTGTCGGAC
TrpPheSerG lyLeuLeuVa lProLysVal AspGluArgL ysThrAlaTr

GGGTGAACGC AATGGGCAGA AGCGTTCGCG GCGCCGTGGC ACTCGGGCAG   250
CCCACTTGCG TTACCCGTCT TCGCAAGCGC CGCGGCACCG TGAGCCCGTC
pGlyGluArg AsnGlyGlnL ysArgSerAr gArgArgGly ThrArgAlaG

GTGGCTTCTG CACGCCCCGC TATATGAGCT GCCTCCGGGA TGCAGAGCCA   300
CACCGAAGAC GTGCGGGGCG ATATACTCGA CGGAGGCCCT ACGTCTCGGT
lyGlyPheCy sThrProArg TyrMetSerC ysLeuArgAs pAlaGluPro

CCCAGCCCCA CCCCTGCGGG CCCCCCTCGG TGCCCCTGGC AGGATGACGC   350
GGGTCGGGGT GGGGACGCCC GGGGGAGCC ACGGGACCG TCCTACTGCG
ProSerProT hrProAlaGl yProProArg CysProTrpG lnAspAspAl

CTTCATCCGG AGGGGCGGCC CAGGCAAGGG CAAGGAGCTG GGGCTGCGGG   400
GAAGTAGGCC TCCCCGCCGG GTCCGTTCCC GTTCCTCGAC CCCGACGCCC
aPheIleArg ArgGlyGlyP roGlyLysGl yLysGluLeu GlyLeuArgA

CAGTGGCCCT GGGCTTCGAG GATACCGAGG TGACAACGAC AGCGGGCGGG   450
GTCACCGGGA CCCGAAGCTC CTATGGCTCC ACTGTTGCTG TCGCCCGCCC
laValAlaLe uGlyPheGlu AspThrGluV alThrThrTh rAlaGlyGly

ACGGCTGAGG TGGCGCCCGA CGCGGTGCCC AGGAGTGGGA GATCCTGCTG   500
TGCCGACTCC ACCGCGGGCT GCGCCACGGG TCCTCACCCT CTAGGACGAC
ThrAlaGluV alAlaProAs pAlaValPro ArgSerGlyA rgSerCysTr

GCGCCGTCTG GTGCAGGTGT TCCAGTCGAA GCAGTTCCGT TCGGCCAAGC   550
CGCGGCAGAC CACGTCCACA AGGTCAGCTT CGTCAAGGCA AGCCGGTTCG
pArgArgLeu ValGlnValP heGlnSerLy sGlnPheArg SerAlaLysL

TGGAGCACCT GTACCAGCGG TACTTCTTCC AGATGAACCA GAGCAGCCTG   600
ACCTCGTGGA CATGGTCGCC ATGAAGAAGG TCTACTTGGT CTCGTCGGAC
euGluHisLe uTyrGlnArg TyrPhePheG lnMetAsnGl nSerSerLeu
```

FIG. 1B

```
ACGCTGCTGA TGGCGGTGCT GGTGCTGCTC ACAGCGGTGC TGCTGGCTTT    650
TGCGACGACT ACCGCCACGA CCACGACGAG TGTCGCCACG ACGACCGAAA
ThrLeuLeuM etAlaValLe uValLeuLeu ThrAlaValL euLeuAlaPh

CCACGCCGCA CCCGCCCGCC CTCAGCCTGC CTATGTGGCA CTGTTGGCCT    700
GGTGCGGCGT GGGCGGGCGG GAGTCGGACG GATACACCGT GACAACCGGA
eHisAlaAla ProAlaArgP roGlnProAl aTyrValAla LeuLeuAlaC

GTGCCGCCGC CCTGTTCGTG GGGCTCATGG TGGTGTGTAA CCGGCATAGC    750
CACGGCGGCG GGACAAGCAC CCCGAGTACC ACCACACATT GGCCGTATCG
ysAlaAlaAl aLeuPheVal GlyLeuMetV alValCysAs nArgHisSer

TTCCGCCAGG ACTCCATGTG GGTGGTGAGC TACGTGGTGC TGGGCATCCT    800
AAGGCGGTCC TGAGGTACAC CCACCACTCG ATGCACCACG ACCCGTAGGA
PheArgGlnA spSerMetTr pValValSer TyrValValL euGlyIleLe

GGCGGCAGTG CAGGTCGGGG GCGCTCTCGC AGCAGACCCG CGCAGCCCCT    850
CCGCCGTCAC GTCCAGCCCC CGCGAGAGCG TCGTCTGGGC GCGTCGGGGA
uAlaAlaVal GlnValGlyG lyAlaLeuAl aAlaAspPro ArgSerProS

CTGCGGGCCT CTGGTGCCCT GTGTTCTTTG TCTACATCGC CTACACGCTC    900
GACGCCCGGA GACCACGGGA CACAAGAAAC AGATGTAGCG GATGTGCGAG
erAlaGlyLe uTrpCysPro ValPhePheV alTyrIleAl aTyrThrLeu

CTCCCCATCC GCATGCGGGC TGCCGTCCTC AGCGGCCTGG GCCTCTCCAC    950
GAGGGGTAGG CGTACGCCCG ACGGCAGGAG TCGCCGGACC CGGAGAGGTG
LeuProIleA rgMetArgAl aAlaValLeu SerGlyLeuG lyLeuSerTh

CTTGCATTTG ATCTTGGCCT GGCAACTTAA CCGTGGTGAT GCCTTCCTCT   1000
GAACGTAAAC TAGAACCGGA CCGTTGAATT GGCACCACTA CGGAAGGAGA
rLeuHisLeu IleLeuAlaT rpGlnLeuAs nArgGlyAsp AlaPheLeuT

GGAAGCAGCT CGGTGCCAAT GTGCTGCTGT TCCTCTGCAC CAACGTCATT   1050
CCTTCGTCGA GCCACGGTTA CACGACGACA AGGAGACGTG GTTGCAGTAA
rpLysGlnLe uGlyAlaAsn ValLeuLeuP heLeuCysTh rAsnValIle

GGCATCTGCA CACACTATCC AGCAGAGGTG TCTCAGCGCC AGGCCTTTCA   1100
CCGTAGACGT GTGTGATAGG TCGTCTCCAC AGAGTCGCGG TCCGGAAAGT
GlyIleCysT hrHisTyrPr oAlaGluVal SerGlnArgG lnAlaPheGl

GGAGACCCGC GGTTACATCC AGGCCCGGCT CCACCTGCAG CATGAGAATC   1150
CCTCTGGGCG CCAATGTAGG TCCGGGCCGA GGTGGACGTC GTACTCTTAG
nGluThrArg GlyTyrIleG lnAlaArgLe uHisLeuGln HisGluAsnA

GGCAGCAGGA GCGGCTGCTG CTGTCGGTAT TGCCCCAGCA CGTTGCCATG   1200
CCGTCGTCCT CGCCGACGAC GACAGCCATA ACGGGGTCGT GCAACGGTAC
rgGlnGlnGl uArgLeuLeu LeuSerValL euProGlnHi sValAlaMet
```

FIG. IC

```
GAGATGAAAG  AAGACATCAA  CACAAAAAAA  GAAGACATGA  TGTTCCACAA  1250
CTCTACTTTC  TTCTGTAGTT  GTGTTTTTTT  CTTCTGTACT  ACAAGGTGTT
GluMetLysG  luAspIleAs  nThrLysLys  GluAspMetM  etPheHisLy

GATCTACATA  CAGAAGCATG  ACAATGTCAG  CATCCTGTTT  GCAGACATTG  1300
CTAGATGTAT  GTCTTCGTAC  TGTTACAGTC  GTAGGACAAA  CGTCTGTAAC
sIleTyrIle  GlnLysHisA  spAsnValSe  rIleLeuPhe  AlaAspIleG

AGGGCTTCAC  CAGCCTGGCA  TCCCAGTGCA  CTGCGCAGGA  GCTGGTCATG  1350
TCCCGAAGTG  GTCGGACCGT  AGGGTCACGT  GACGCGTCCT  CGACCAGTAC
luGlyPheTh  rSerLeuAla  SerGlnCysT  hrAlaGlnGl  uLeuValMet

ACCCTGAATG  AGCTCTTTGC  CCGGTTTGAC  AAGCTGGCTG  CGGAGAATCA  1400
TGGGACTTAC  TCGAGAAACG  GGCCAAACTG  TTCGACCGAC  GCCTCTTAGT
ThrLeuAsnG  luLeuPheAl  aArgPheAsp  LysLeuAlaA  laGluAsnHi

CTGCCTGAGG  ATCAAGATCT  TGGGGACTG   TTACTACTGT  GTGTCAGGGC  1450
GACGGACTCC  TAGTTCTAGA  ACCCCCTGAC  AATGATGACA  CACAGTCCCG
sCysLeuArg  IleLysIleL  euGlyAspCy  sTyrTyrCys  ValSerGlyL

TGCCGGAGGC  CCGGGCCGAC  CATGCCCACT  GCTGTGTGGA  GATGGGGGTA  1500
ACGGCCTCCG  GGCCCGGCTG  GTACGGGTGA  CGACACACCT  CTACCCCCAT
euProGluAl  aArgAlaAsp  HisAlaHisC  ysCysValGl  uMetGlyVal

GACATGATTG  AGGCCATCTC  GCTGGTACGT  GAGGTGACAG  GTGTGAATGT  1550
CTGTACTAAC  TCCGGTAGAG  CGACCATGCA  CTCCACTGTC  CACACTTACA
AspMetIleG  luAlaIleSe  rLeuValArg  GluValThrG  lyValAsnVa

GAACATGCGC  GTGGGCATCC  ACAGCGGGCG  CGTGCACTGC  GGCGTCCTTG  1600
CTTGTACGCG  CACCCGTAGG  TGTCGCCCGC  GCACGTGACG  CCGCAGGAAC
lAsnMetArg  ValGlyIleH  isSerGlyAr  gValHisCys  GlyValLeuG

GCTTGCGGAA  ATGGCAGTTC  GATGTGTGGT  CCAATGATGT  GACCCTGGCC  1650
CGAACGCCTT  TACCGTCAAG  CTACACACCA  GGTTACTACA  CTGGGACCGG
lyLeuArgLy  sTrpGlnPhe  AspValTrpS  erAsnAspVa  lThrLeuAla

AACCACATGG  AGGCAGGAGG  CCGGGCTGGC  CGCATCCACA  TCACTCGGGC  1700
TTGGTGTACC  TCCGTCCTCC  GGCCCGACCG  GCGTAGGTGT  AGTGAGCCCG
AsnHisMetG  luAlaGlyGl  yArgAlaGly  ArgIleHisI  leThrArgAl

AACACTGCAG  TACCTGAACG  GGACTACGA   GGTGGAGCCA  GGCCGTGGTG  1750
TTGTGACGTC  ATGGACTTGC  CCCTGATGCT  CCACCTCGGT  CCGGCACCAC
aThrLeuGln  TyrLeuAsnG  lyAspTyrGl  uValGluPro  GlyArgGlyG

GCGAGCGCAA  CGCGTACCTC  AAGGAGCAGC  ACATTGAGAC  TTTCCTCATC  1800
CGCTCGCGTT  GCGCATGGAG  TTCCTCGTCG  TGTAACTCTG  AAAGGAGTAG
lyGluArgAs  nAlaTyrLeu  LysGluGlnH  isIleGluTh  rPheLeuIle
```

FIG. 1D

```
CTGGGCGCCA GCCAGAAACG GAAAGAGGAG AAGGCCATGC TGGCCAAGCT   1850
GACCCGCGGT CGGTCTTTGC CTTTCTCCTC TTCCGGTACG ACCGGTTCGA
LeuGlyAlaS erGlnLysAr gLysGluGlu LysAlaMetL euAlaLysLe

GCAGCGGACT CGGGCCAACT CCATGGAAGG GCTGATGCCG CGCTGGGTTC   1900
CGTCGCCTGA GCCCGGTTGA GGTACCTTCC CGACTACGGC GCGACCCAAG
uGlnArgThr ArgAlaAsnS erMetGluGl yLeuMetPro ArgTrpValP

CTGATCGTGC CTTCTCCCGG ACCAAGGACT CCAAGGCCTT CCGCCAGATG   1950
GACTAGCACG GAAGAGGGCC TGGTTCCTGA GGTTCCGGAA GGCGGTCTAC
roAspArgAl aPheSerArg ThrLysAspS erLysAlaPh eArgGlnMet

GGCATTGATG ATTCCAGCAA AGACAACCGG GGCACCCAAG ATGCCCTGAA   2000
CCGTAACTAC TAAGGTCGTT TCTGTTGGCC CCGTGGGTTC TACGGGACTT
GlyIleAspA spSerSerLy sAspAsnArg GlyThrGlnA spAlaLeuAs

CCCTGAGGAT GAGGTGGATG AGTTCCTGAG CCGTGCCATC GATGCCCGCA   2050
GGGACTCCTA CTCCACCTAC TCAAGGACTC GGCACGGTAG CTACGGGCGT
nProGluAsp GluValAspG luPheLeuSe rArgAlaIle AspAlaArgS

GCATTGATCA GCTGCGGAAG GACCATGTGC GCCGGTTTCT GCTCACCTTC   2100
CGTAACTAGT CGACGCCTTC CTGGTACACG CGGCCAAAGA CGAGTGGAAG
erIleAspGl nLeuArgLys AspHisValA rgArgPheLe uLeuThrPhe

CAGAGAGAGG ATCTTGAGAA GAAGTACTCC CGGAAGGTGG ATCCCCGCTT   2150
GTCTCTCTCC TAGAACTCTT CTTCATGAGG GCCTTCCACC TAGGGGCGAA
GlnArgGluA spLeuGluLy sLysTyrSer ArgLysValA spProArgPh

CGGAGCCTAC GTTGCCTGTG CCCTGTTGGT CTTCTGCTTC ATCTGCTTCA   2200
GCCTCGGATG CAACGGACAC GGGACAACCA GAAGACGAAG TAGACGAAGT
eGlyAlaTyr ValAlaCysA laLeuLeuVa lPheCysPhe IleCysPheI

TCCAGCTTCT CATCTTCCCA CACTCCACCC TGATGCTTGG GATCTATGCC   2250
AGGTCGAAGA GTAGAAGGGT GTGAGGTGGG ACTACGAACC CTAGATACGG
leGlnLeuLe uIlePhePro HisSerThrL euMetLeuGl yIleTyrAla

AGCATCTTCC TGCTGCTGCT AATCACCGTG CTGATCTGTG CTGTGTACTC   2300
TCGTAGAAGG ACGACGACGA TTAGTGGCAC GACTAGACAC GACACATGAG
SerIlePheL euLeuLeuLe uIleThrVal LeuIleCysA laValTyrSe

CTGTGGTTCT CTGTTCCCTA AGGCCCTGCA ACGTCTGTCC CGCAGCATTG   2350
GACACCAAGA GACAAGGGAT TCCGGGACGT TGCAGACAGG GCGTCGTAAC
rCysGlySer LeuPheProL ysAlaLeuGl nArgLeuSer ArgSerIleV

TCCGCTCACG GGCACATAGC ACCGCAGTTG GCATCTTTTC CGTCCTGCTT   2400
AGGCGAGTGC CCGTGTATCG TGGCGTCAAC CGTAGAAAAG GCAGGACGAA
alArgSerAr gAlaHisSer ThrAlaValG lyIlePheSe rValLeuLeu
```

FIG. 1E

```
GTGTTTACTT CTGCCATTGC CAACATGTTC ACCTGTAACC ACACCCCCAT  2450
CACAAATGAA GACGGTAACG GTTGTACAAG TGGACATTGG TGTGGGGGTA
ValPheThrS erAlaIleAl aAsnMetPhe ThrCysAsnH isThrProIl

ACGGAGCTGT GCAGCCCGGA TGCTGAATTT AACACCTGCT GACATCACTG  2500
TGCCTCGACA CGTCGGGCCT ACGACTTAAA TTGTGGACGA CTGTAGTGAC
eArgSerCys AlaAlaArgM etLeuAsnLe uThrProAla AspIleThrA

CCTGCCACCT GCAGCAGCTC AATTACTCTC TGGGCCTGGA TGCTCCCCTG  2550
GGACGGTGGA CGTCGTCGAG TTAATGAGAG ACCCGGACCT ACGAGGGGAC
laCysHisLe uGlnGlnLeu AsnTyrSerL euGlyLeuAs pAlaProLeu

TGTGAGGGCA CCATGCCCAC CTGCAGCTTT CCTGAGTACT TCATCGGGAA  2600
ACACTCCCGT GGTACGGGTG GACGTCGAAA GGACTCATGA AGTAGCCCTT
CysGluGlyT hrMetProTh rCysSerPhe ProGluTyrP heIleGlyAs

CATGCTGCTG AGTCTCTTGG CCAGCTCTGT CTTCCTGCAC ATCAGCAGCA  2650
GTACGACGAC TCAGAGAACC GGTCGAGACA GAAGGACGTG TAGTCGTCGT
nMetLeuLeu SerLeuLeuA laSerSerVa lPheLeuHis IleSerSerI

TCGGGAAGTT GGCCATGATC TTTGTCTTGG GGCTCATCTA TTTGGTGCTG  2700
AGCCCTTCAA CCGGTACTAG AAACAGAACC CCGAGTAGAT AAACCACGAC
leGlyLysLe uAlaMetIle PheValLeuG lyLeuIleTy rLeuValLeu

CTTCTGCTGG GTCCCCCAGC CACCATCTTT GACAACTATG ACCTACTGCT  2750
GAAGACGACC CAGGGGGTCG GTGGTAGAAA CTGTTGATAC TGGATGACGA
LeuLeuLeuG lyProProAl aThrIlePhe AspAsnTyrA spLeuLeuLe

TGGCGTCCAT GGCTTGGCTT CTTCCAATGA GACCTTTGAT GGGCTGGACT  2800
ACCGCAGGTA CCGAACCGAA GAAGGTTACT CTGGAAACTA CCCGACCTGA
uGlyValHis GlyLeuAlaS erSerAsnGl uThrPheAsp GlyLeuAspC

GTCCAGCTGC AGGGAGGGTG GCCCTCAAAT ATATGACCCC TGTGATTCTG  2850
CAGGTCGACG TCCCTCCCAC CGGGAGTTTA TATACTGGGG ACACTAAGAC
ysProAlaAl aGlyArgVal AlaLeuLysT yrMetThrPr oValIleLeu

CTGGTGTTTG CGCTGGCGCT GTATCTGCAT GCTCAGCAGG TGGAGTCGAC  2900
GACCACAAAC GCGACCGCGA CATAGACGTA CGAGTCGTCC ACCTCAGCTG
LeuValPheA laLeuAlaLe uTyrLeuHis AlaGlnGlnV alGluSerTh

TGCCCGCCTA GACTTCCTCT GGAAACTACA GGCAACAGGG GAGAAGGAGG  2950
ACGGGCGGAT CTGAAGGAGA CCTTTGATGT CCGTTGTCCC CTCTTCCTCC
rAlaArgLeu AspPheLeuT rpLysLeuGl nAlaThrGly GluLysGluG

AGATGGAGGA GCTACAGGCA TACAACCGGA GGCTGCTGCA TAACATTCTG  3000
TCTACCTCCT CGATGTCCGT ATGTTGGCCT CCGACGACGT ATTGTAAGAC
luMetGluGl uLeuGlnAla TyrAsnArgA rgLeuLeuHi sAsnIleLeu
```

FIG. 1F

```
CCCAAGGACG TGGCGGCCCA CTTCCTGGCC CGGGAGCGCC GCAATGATGA   3050
GGGTTCCTGC ACCGCCGGGT GAAGGACCGG GCCCTCGCGG CGTTACTACT
ProLysAspV alAlaAlaHi sPheLeuAla ArgGluArgA rgAsnAspGl

ACTCTACTAT CAGTCGTGTG AGTGTGTGGC TGTTATGTTT GCCTCCATTG   3100
TGAGATGATA GTCAGCACAC TCACACACCG ACAATACAAA CGGAGGTAAC
uLeuTyrTyr GlnSerCysG luCysValAl aValMetPhe AlaSerIleA

CCAACTTCTC TGAGTTCTAT GTGGAGCTGG AGGCAAACAA TGAGGGTGTC   3150
GGTTGAAGAG ACTCAAGATA CACCTCGACC TCCGTTTGTT ACTCCCACAG
laAsnPheSe rGluPheTyr ValGluLeuG luAlaAsnAs nGluGlyVal

GAGTGCCTGC GGCTGCTCAA CGAGATCATC GCTGACTTTG ATGAGATTAT   3200
CTCACGGACG CCGACGAGTT GCTCTAGTAG CGACTGAAAC TACTCTAATA
GluCysLeuA rgLeuLeuAs nGluIleIle AlaAspPheA spGluIleIl

CAGCGAGGAG CGGTTCCGGC AGCTGGAAAA GATCAAGACG ATTGGTAGCA   3250
GTCGCTCCTC GCCAAGGCCG TCGACCTTTT CTAGTTCTGC TAACCATCGT
eSerGluGlu ArgPheArgG lnLeuGluLy sIleLysThr IleGlySerT

CCTACATGGC TGCCTCAGGG CTGAACGCCA GCACCTACGA TCAGGTGGGC   3300
GGATGTACCG ACGGAGTCCC GACTTGCGGT CGTGGATGCT AGTCCACCCG
nrTyrMetAl aAlaSerGly LeuAsnAlaS erThrTyrAs pGlnValGly

CGCTCCCACA TCACTGCCCT GGCTGACTAC GCCATGCGGC TCATGGAGCA   3350
GCGAGGGTGT AGTGACGGGA CCGACTGATG CGGTACGCCG AGTACCTCGT
ArgSerHisI leThrAlaLe uAlaAspTyr AlaMetArgL euMetGluGl

GATGAAGCAC ATCAATGAGC ACTCCTTCAA CAATTTCCAG ATGAAGATTG   3400
CTACTTCGTG TAGTTACTCG TGAGGAAGTT GTTAAAGGTC TACTTCTAAC
nMetLysHis IleAsnGluH isSerPheAs nAsnPheGln MetLysIleG

GGCTGAACAT GGGCCCAGTC GTGGCAGGTG TCATCGGGGC TCGGAAGCCA   3450
CCGACTTGTA CCCGGGTCAG CACCGTCCAC AGTAGCCCCG AGCCTTCGGT
lyLeuAsnMe tGlyProVal ValAlaGlyV alIleGlyAl aArgLysPro

CAGTATGACA TCTGGGGGAA CACAGTGAAT GTCTCTAGTC GTATGGACAG   3500
GTCATACTGT AGACCCCCTT GTGTCACTTA CAGAGATCAG CATACCTGTC
GlnTyrAspI leTrpGlyAs nThrValAsn ValSerSerA rgMetAspSe

CACGGGGGTC CCCGACCGAA TCCAGGTGAC CACGGACCTG TACCAGGTTC   3550
GTGCCCCCAG GGGCTGGCTT AGGTCCACTG GTGCCTGGAC ATGGTCCAAG
rThrGlyVal ProAspArgI leGlnValTh rThrAspLeu TyrGlnValL

TAGCTGCCAA GGGCTACCAG CTGGAGTGTC GAGGGGTGGT CAAGGTGAAG   3600
ATCGACGGTT CCCGATGGTC GACCTCACAG CTCCCCACCA GTTCCACTTC
euAlaAlaLy sGlyTyrGln LeuGluCysA rgGlyValVa lLysValLys
```

FIG. 1G

```
GGCAAGGGGG AGATGACCAC CTACTTCCTC AATGGGGCC CCAGCAGTTA 3650
CCGTTCCCCC TCTACTGGTG GATGAAGGAG TTACCCCGG GGTCGTCAAT
GlyLysGlyG luMetThrTh rTyrPheLeu AsnGlyGlyP roSerSer

ACAGGGCCCA GCCACAAATT CAGCTGAAGG GACCAAGGTG GGCATTGAGT 3700
TGTCCCGGGT CGGTGTTTAA GTCGACTTCC CTGGTTCCAC CCGTAACTCA

GGACTCTGTG CTCACTGGGT GGAGCTGTGG CAGGGGGCAC TGAGCCTCCA 3750
CCTGAGACAC GAGTGACCCA CCTCGACACC GTCCCCCGTG ACTCGGAGGT

GACCCTGCTA ACCACAAAAG GAACATCCC AGCAGGCTGT GCTTGGATCA 3800
CTGGGACGAT TGGTGTTTTC CCTTGTAGGG TCGTCCGACA CGAACCTAGT

TGCTCGTCTG CCCTCAAGCT GGAAAACAAG GGGCTACCTA CCGAGAGGAT 3850
ACGAGCAGAC GGGAGTTCGA CCTTTTGTTC CCCGATGGAT GGCTCTCCTA

TATGCAAGTG ACTTTCTTTC TTACTTGGGG TAGGGCTGTT CCCTCTCCAA 3900
ATACGTTCAC TGAAAGAAAG AATGAACCCC ATCCCGACAA GGGAGAGGTT

TCTTCCAGCC TTTGGGAGCA GGGGAGGGGT CAGTAGCAGA AGCAGAGGGA 3950
AGAAGGTCGG AAACCCTCGT CCCCTCCCCA GTCATCGTCT TCGTCTCCCT

GGCCTCTTGC CTGAGGGATT AAAATGGCAG CTTGCCATGC CTACCCTTCC 4000
CCGGAGAACG GACTCCCTAA TTTTACCGTC GAACGGTACG GATGGGAAGG

CTGTCTGTCT GGGCAGCAGG TTCAGGGCTG AGCCCTTCTT TTCCCTCTTT 4050
GACAGACAGA CCCGTCGTCC AAGTCCCGAC TCGGGAAGAA AAGGGAGAAA

TTTCCTGGGA ATATTTTGTA CAATATTTTG TACAAAGACA GGCATGAGGA 4100
AAAGGACCCT TATAAAACAT GTTATAAAAC ATGTTTCTGT CCGTACTCCT

GTGCCTATTC CATGCTTGCC TTTGCAATAC CTGCATCCCC AGCACTGGTC 4150
CACGGATAAG GTACGAACGG AAACGTTATG GACGTAGGGG TCGTGACCAG

CTGGGCACTT CCCCACCCCA GCCAGGTGTC CCTCCTATGC ACAGAGCAGA 4200
GACCCGTGAA GGGGTGGGGT CGGTCCACAG GGAGGATACG TGTCTCGTCT
```

FIG. 1H

```
GGAGGGAGAA GCTCTGGGGA GCCAGCTTTG GCCATATTTC AGGAGAATGT   4250
CCTCCCTCTT CGAGACCCCT CGGTCGAAAC CGGTATAAAG TCCTCTTACA

TTCCATGTGC CAAATCTTAG TCCCATGATC TGTCCCCAAA GGGGAACAAA   4300
AAGGTACACG GTTTAGAATC AGGGTACTAG ACAGGGGTTT CCCCTTGTTT

GGGACCTCTG ACAGCTTAGA TTTAGCCCCA GTTCCTGCAC GCTCCAGGGA   4350
CCCTGGAGAC TGTCGAATCT AAATCGGGGT CAAGGACGTG CGAGGTCCCT

ACGGGGTGTC TGGCCTCACT GGTACTGTGA AAAATGCTCA GAGAGCAAGC   4400
TGCCCCACAG ACCGGAGTGA CCATGACACT TTTTACGAGT CTCTCGTTCG

CTGTGTGTGG GGATGTCAGG TCAGGAGCTG GAAGTTCACC TGCAGGTGCC   4450
GACACACACC CCTACAGTCC AGTCCTCGAC CTTCAAGTGG ACGTCCACGG

AAAGAGCAGG CCGGCCAGGG CTGGGGCAGT GCCAGACTCT GATCTGAGGA   4500
TTTCTCGTCC GGCCGGTCCC GACCCCGTCA CGGTCTGAGA CTAGACTCCT

CCCCGTCGGG GTCCAGATCA GGTCACTCTG CCCCAGTGCT CTCTTGCTGT   4550
GGGGCAGCCC CAGGTCTAGT CCAGTGAGAC GGGGTCACGA GAGAACGACA

CTGCTGACAA GGGGGCATGG AGCATCTCTT CCTCTTCTGT TGCCAAATAG   4600
GACGACTGTT CCCCCGTACC TCGTAGAGAA GGAGAAGACA ACGGTTTATC

AAAAGGGTCA GGGCATGGAG AAAGGTGACC CTGATCCCAA ACCTGCCCTC   4650
TTTTCCCAGT CCCGTACCTC TTTCCACTGG GACTAGGGTT TGGACGGGAG

CCAAGTCTCT GGTGTTGGGG AGGGCCCGTG TGTTTGTGTA ACTGTGTGTG   4700
GGTTCAGAGA CCACAACCCC TCCCGGGCAC ACAAACACAT TGACACACAC

CATGTTGGTC TTTGTGTGCA TATCTGTTTT CCAGGTCTAT GTGAGTCCTT   4750
GTACAACCAG AAACACACGT ATAGACAAAA GGTCCAGATA CACTCAGGAA

GTGCTCCTGC TCCTCAGCTC TCCACCCCAG GTTGCCTCTC TCCTGTGGGC   4800
CACGAGGACG AGGAGTCGAG AGGTGGGGTC CAACGGAGAG AGGACACCCG
```

FIG. 11

```
CTCTGTCTTC TGGGAATAAA GCAGGGTTTC CTACTTCAGG GGATGTAGAG  4850
GAGACAGAAG ACCCTTATTT CGTCCCAAAG GATGAAGTCC CCTACATCTC

AGATGCCCAG GTTGCACAGG AGTGGGATGG GGTGTGGTAG CAAAAGGAGG  4900
TCTACGGGTC CAACGTGTCC TCACCCTACC CCACACCATC GTTTTCCTCC

GAGAGGAGTC CTTTTTGTGC CAAATCCCTA AGTGCCGTTC GG           4942
CTCTCCTCAG GAAAAACACG GTTTAGGGAT TCACGGCAAG CC
```

CLONING AND CHARACTERIZATION OF A HUMAN ADENYLYL CYCLASE

RELATED APPLICATIONS

This application is a divisional of U.S. patent application Ser. No. 10/201,000, filed Jul. 24, 2002, now U.S. Pat. No. 6,864,081 issued Mar. 8, 2005 which is a divisional of U.S. patent application Ser. No. 09/474,076, filed Dec. 29, 1999, now U.S. Pat. No. 6,465,237, which is a continuation of International Application Serial Number PCT/US98/13694, filed Jul. 1, 1998, which designated the U.S. and claims priority to U.S. Non-Provisional application Ser. No. 08/886,550, filed Jul. 1, 1997, which has been converted to U.S. Provisional Application Ser. No. 60/070,904, filed Jul. 1, 1997, now abandoned, all of which are herein incorporated in their entirety.

FIELD OF THE INVENTION

This invention relates to DNA encoding a human adenylyl cyclase. This invention also relates to the adenylyl cyclase encoded by that DNA. Referred to herein as the human type VI adenylyl cyclase (hAC6) polypeptide, this enzyme can be used as a tool to screen for agonists and antagonists that can either stimulate or inhibit type VI adenylyl cyclase activity. Such compounds have therapeutic utility in treating (1) diseases that are caused by aberrant activity of this enzyme and (2) diseases whose symptoms can be ameliorated by stimulating or inhibiting the activity of type VI adenylyl cyclase.

The present invention also relates to the isolated entire human gene encoding the human type VI adenylyl cyclase, methods for the recombinant production of purified human type VI adenylyl cyclase and the proteins made by these methods, antibodies against the whole human type VI adenylyl cyclase or regions thereof, vectors, nucleotide probes, and host cells transformed by genes encoding polypeptides having human type VI adenylyl cyclase activity, along with diagnostic and therapeutic uses for these various reagents.

BACKGROUND OF THE INVENTION

Adenylyl cyclases direct the intracellular synthesis of the primary second messenger, cyclic-3',5'-adenosine monophosphate (cAMP), by converting ATP to cAMP, principally in response to a diverse family of membrane spanning, G-protein coupled receptors, each activated by its own extracellular hormone or protease. Signal transduction for G-protein coupled receptors occurs through a coupled heterotrimeric G protein complex composed of the alpha ($G_\alpha$), and beta/gamma ($G_{\beta\gamma}$) subunits. Upon receptor stimulation, $G_\alpha$ exchanges GTP for GDP, dissociates from both $G_{\beta\gamma}$ and the receptor, and proceeds to directly regulate various effectors, including adenylyl cyclase. Multiple families of $G_\alpha$ proteins have been identified, two of which are named for their effects on regulating adenylyl cyclase activity ($G_{\alpha s}$ family stimulates all adenylyl cyclases, while $G_{\alpha i}$ family inhibits most but not all of the adenylyl cyclases). Each of these $G_\alpha$ proteins has its own tissue distribution, and subset of coupled receptors, which favors receptor specific regulation of adenylyl cyclase.

Additional studies have suggested other means by which adenylyl cyclase activity may be regulated within tissues. This concept is derived from findings that a number of adenylyl cyclase isoforms exist, each with their own gene locus, distinct set of responses to intracellular signals and unique tissue distribution. To date, nine separate isoforms (Types I–IX) have been characterized, principally from rodents, each with its own regulatory properties and tissue specific distribution.

The structure of adenylyl cyclases has been greatly studied and the putative domains given standard nomenclature. Topographically, the adenylyl cyclase isoforms are similar, having two six-transmembrane spanning regions associated with an intracellular N-terminus, a large cytoplasmic loop (ICD III, more commonly referred to as "$C_1$") and an intracellular C-terminus (more commonly referred to as "$C_2$"). The transmembrane region between the N-terminus and the $C_1$ loop is commonly referred to as "M1". The M1 region has three extracellular domains (ECD I, II and III), two intracellular domains (ICD I and II) and six transmembrane domains (TM I, II, III, IV, V and VI). The region between the $C_1$ loop and the C-terminus is referred to as "M2". The M2 region has three extracellular domains (ECD IV, V and VI), two intracellular domains (ICD IV and V) and six transmembrane domains (TM VII, VIII, IX, X, XI and XII). The N-terminus is commonly divided into two regions, designated "$N_1$" and "$N_2$". The large $C_1$ cytoplasmic loop is also divided into two regions, a long "$C_{1a}$" region and a shorter "$C_{1b}$" region. Lastly, the C-terminus is divided into a long "$C_{2a}$" region and a shorter "$C_{2b}$" region. An extensive discussion of these regions can be found in Broach, et al., WO 95/30012, which is incorporated herein by reference. The amino acid sequence of the $C_{1a}$ and $C_{2a}$ regions are conserved among the different isoforms. On the other hand, the N-terminus, $C_{1b}$ and $C_{2b}$ regions show the most diversity among the various isoforms.

Based on sequence and functional similarities, these isoforms fall into six distinct classes of adenylyl cyclases. Type VI is in the same class as type V, showing sequence similarity even in the transmembrane regions where the greatest level of divergence is noted among the isoforms. Type V is predominantly expressed in heart and brain tissue. Type VI has a somewhat broader distribution, but its dominant expression is also in heart and brain tissue. Type VI, like type V, has a relatively longer N-terminus and relatively shorter C-terminus, lacking the $C_{2b}$ region, than the other isoforms.

Diversity in activities, and differences in distribution and prevalence of adenylyl cyclase isoforms, may contribute to tissue specific regulation of cAMP levels. It is expected that by taking advantage of distinct structural and biochemical differences between different adenylyl cyclases, isoform specific or selective modulators can be discovered. This, in conjunction with knowledge of the proportion and distribution of each isoform in select tissues provides a means by which one can develop either tissue specific, or selective pharmacological agents since it is expected that isoform specific modulators would have tissue specificity related to the distribution of that isoform.

Key to the development of selective pharmacological agents is information pertaining to the tissue specific distribution and prevalence of each isoform. To date most of this information is available for isoform mRNA levels in a handful of non-human mammals, although some select mRNA (e.g. Type V) have been measured for many human tissues. Acquiring information on protein isoform distribution in human tissues is considered an important aspect of pharmaceutical research in this area, since this could either strengthen existing target information or point to different isoforms, when compared with mRNA data.

To date, only three full length human adenylyl cyclase isoforms have been cloned: Type II adenylyl cyclase (Stengel, et al., *Hum. Genet.* 90: 126–130 (1992)), Type VII adenylyl cyclase (Nomura, et al., *DNA Research* 1: 27–35 (1994)) and Type VIII adenylyl cyclase (Defer, et al., *FEBS Letters* 351: 109–113 (1994)).

Type VI has been cloned from mouse NCB-20 cells (Yoshimura, et al., *Proc. Natl. Acad. Sci. USA* 89: 6716–6720 (1992)) and canine heart (Katsushika, et al., *Proc. Natl. Acad. Sci. USA* 89: 8774–8778 (1992) and Ishikawa, U.S. Pat. No. 5,334,521). The human isoform has not been cloned until now.

SUMMARY OF THE INVENTION

One aspect of the invention is an isolated and purified human type VI adenylyl cyclase (hAC6) polypeptide comprising the amino acid sequence of FIG. 1 (SEQ ID NO:2).

Another aspect of the invention is an isolated and purified nucleic acid encoding for the hAC6 polypeptide.

Yet another aspect of the invention is an isolated and purified nucleic acid comprising the nucleotide sequence of FIG. 1 (SEQ ID NO:1), which encodes a biologically active hAC6 polypeptide, or fragment thereof.

Still another aspect of the invention is an isolated and purified nucleic acid comprising the nucleotide sequence of FIG. 1 (SEQ ID NO:1), which encodes a biologically active soluble hAC6 peptide fragment.

Another aspect of the present invention also relates to the human gene encoding human type VI adenylyl cyclase, which has both diagnostic and therapeutic uses as are described below. Included within this invention are proteins or peptides having substantial homology with proteins or peptides comprising the amino acid sequence of FIG. 1 or encoded by a gene having substantial homology with the nucleotide sequence of FIG. 1, and which exhibit the same characteristics of human type VI adenylyl cyclase.

Yet another aspect of the invention is a method of producing hAC6 which comprises incorporating a nucleic acid having the nucleotide sequence of FIG. 1 (SEQ ID NO:1) into an expression vector, transforming a host cell with the vector and culturing the transformed host cell under conditions which result in expression of the gene.

BRIEF DESCRIPTION OF THE DRAWINGS

FIG. 1(A-I) is the DNA (SEQ ID NO:1) and deduced amino acid sequence (SEQ ID NO:2) of human type VI adenylyl cyclase. The entire coding sequence, as well as portions of the 5' and 3' untranslated sequences, are shown. The whole sequence was done bidirectionally twice by dideoxy sequencing method using Taq polymerase.

DETAILED DESCRIPTION OF THE INVENTION

Definitions

Before proceeding further with a description of the specific embodiments of the present invention, a number of terms will be defined:

The terms "substantially pure" and "isolated" are used herein to describe a protein that has been separated from the native contaminants or components that naturally accompany it. Typically, a monomeric protein is substantially pure when at least about 60 to 70% of a sample exhibits a single polypeptide backbone. Minor variants or chemical modifications typically share approximately the same polypeptide sequence. A substantially pure protein will typically comprise over about 85 to 90% of a protein sample, preferably will comprise at least about 95%, and more preferably will be over about 99% pure. Purity is typically measured on a polyacrylamide gel, with homogeneity determined by staining. For certain purposes, high resolution will be desired and HPLC or a similar means for purification utilized. However, for most purposes, a simple chromatography column or polyacrylamide gel will be used to determine purity. Whether soluble or membrane bound, the present invention provides for substantially pure preparations. Various methods for their isolation from biological material may be devised, based in part upon the structural and functional descriptions contained herein. In addition, a protein that is chemically synthesized or synthesized in a cellular system that is different from the cell from which it naturally originates, will be substantially pure. The term is also used to describe proteins and nucleic acids that have been synthesized in heterologous mammalian cells, bacterial cells such as *E. coli* and other prokaryotes.

As used herein, the terms "hybridization" (hybridizing) and "specificity" (specific for) in the context of nucleotide sequences are used interchangeably. The ability of two nucleotide sequences to hybridize to each other is based upon a degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the conditions of stringency which include temperature, solvent ratios, salt concentrations, and the like. In particular, "selective hybridization" pertains to conditions in which the degree of hybridization of a polynucleotide of the invention to its target would require complete or nearly complete complementarity. The complementarity must be sufficiently high so as to assure that the polynucleotide of the invention will bind specifically to the target relative to binding other nucleic acids present in the hybridization medium. With selective hybridization, complementarity will be 90–100%, preferably 95–100%, more preferably 100%.

"Stringent conditions" are those that (1) employ low ionic strength and high temperature for washing, for example, 0.015 M NaCl/0.0015 M sodium titrate/0.1% NaDodSO$_4$ at 50° C., or (2) employ during hybridization a denaturing agent such as formamide, for example, 50% (vol/vol) formamide with 0.1% bovine serum albumin ("BSA")/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×0.75 M NaCl and 0.075 M sodium citrate ("SSC"), 50 mM sodium phosphate (pH 6.8), 0.1% sodium pyrophosphate, 5× Denhardt's solution, sonicated salmon sperm DNA (50 mg/ml), 0.1% sodium dodecyl sulfate ("SDS"), and 10% dextran sulfate at 42° C., with washes at 42° C. in 0.2×SSC and 0.1% SDS.

"Isolated" nucleic acid will be nucleic acid that is identified and separated from contaminant nucleic acid encoding other polypeptides from the source of nucleic acid. The nucleic acid may be labeled for diagnostic and probe purposes, using any label known and described in the art as useful in connection with diagnostic assays.

PREFERRED EMBODIMENTS

The present invention relates to human type VI adenylyl cyclase, which is referred to herein as "hAC6". FIG. 1 shows the DNA sequence of the clone encoding the hAC6 polypeptide along with the deduced amino acid sequence. As used herein, the terms "hAC6 polypeptide" or "hAC6 enzyme" refer to any adenylyl cyclase sharing a common biological activity with the human type VI adenylyl cyclase contained in the clone described in Example 1. This "common biological activity" includes but is not limited to an effector function or cross-reactive antigenicity.

As indicated above, type VI adenylyl cyclase is in the same isoform class as type VI, being expressed mainly in the heart and brain. As with the other known isoforms, type VI adenylyl cyclase has a similar putative structure: six extracellular domains; five intracellular domains, four small ones and a large cytoplasmic loop; and intracellular amino and carboxy termini.

However, type VI adenylyl cyclase, like type V, is distinguishable over other adenylyl cyclase isoforms in that it has a larger N-terminus and a relatively shorter C-terminus as it lacks the $C_{2b}$ region. In the other mammalian isoforms (types I–V and VII–IX), much of the membrane associated secondary structure is well conserved. Certain portions of the hAC6 polypeptide are similarly conserved.

The scope of the present invention is not limited to the exact sequence of the hAC6 cDNA set forth in FIG. 1 (SEQ ID NO: 1), or the use thereof. The invention contemplates certain modifications to the sequence, including deletions, insertions, and substitutions, such as are well known to those skilled in the art. For example, the invention contemplates replacing one or more codons in the cDNA sequence of FIG. 1, with codons that encode amino acids that are chemically equivalent to the amino acids in the native protein. Chemical equivalency is determined, for example, by one or more of the following characteristics: hydrophobicity or hydrophilicity, charge, size, whether the residue is cyclic or non-cyclic, aromatic or non-aromatic. So, for example, a codon encoding a neutral polar amino acid can be substituted with another codon that encodes a neutral polar residue, with the reasonable expectation of producing a biologically equivalent product.

Amino acid residues can be generally classified into four groups. Acidic residues are hydrophilic and have a negative charge due to loss of $H^+$ at physiological pH. Basic residues are also hydrophilic but have a positive charge due to association with $H^+$ at physiological pH. Neutral nonpolar residues are hydrophobic and are not charged at physiological pH. Neutral polar residues are hydrophilic and are not charged at physiological pH. Amino acid residues can be further classified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

Of the naturally occurring amino acids, aspartic acid and glutamic acid are acidic; arginine and lysine are basic and noncyclic; histidine is basic and cyclic; glycine, serine and cysteine are neutral, polar and small; alanine is neutral, nonpolar and small; threonine, asparagine and glutamine are neutral, polar, large and nonaromatic; tyrosine is neutral, polar, large and aromatic; valine, isoleucine, leucine and methionine are neutral, nonpolar, large and nonaromatic; and phenylalanine and tryptophan are neutral, nonpolar, large and aromatic. Proline, although technically neutral, nonpolar, large, cyclic and nonaromatic, is a special case due to its known effects on the secondary conformation of peptide chains, and is not, therefore, included in this defined group.

There are also commonly encountered amino acids, which are not encoded by the genetic code. These include, by way of example and not limitation: sarcosine, beta-alanine, 2,3-diamino propionic and alpha-aminisobutyric acid which are neutral, nonpolar and small; t-butylalanine, t-butylglycine, N-methylisoleucine, norleucine and cyclohexylalanine which are neutral, nonpolar, large and nonaromatic; ornithine which is basic and noncyclic; cysteic acid which is acidic; citrulline, acetyl lysine, and methionine sulfoxide which are neutral, polar, large and nonaromatic; and phenylglycine, 2-naphthylalanine, β-2-thienylalanine and 1,2,3,4-tetrahydroisoquinoline-3-carboxylic acid which are neutral, nonpolar, large and aromatic.

Ordinarily, the hAC6 polypeptide claimed herein will have an overall amino acid sequence having at least 75% amino acid sequence identity with the hAC6 sequence disclosed in FIG. 1, more preferably at least 80%, even more preferably at least 90%, and most preferably at least 95%. More particularly, the N-terminus, C1b and C2b regions of the hAC6 polypeptide or polypeptide fragment claimed herein, will have an amino acid sequence having at least 90%, and most preferably at least 95% amino acid sequence identity with the hAC6 sequence disclosed in FIG. 1. Identity or homology with a sequence is defined herein as the percentage of amino acid residues in the candidate sequence that are identical with the sequence of the hAC6 polypeptide, after aligning the sequences and introducing gaps, if necessary, to achieve the maximum percent homology, and not considering any conservative substitutions as part of the sequence identity. N-terminal, C-terminal or internal extensions, deletions, or insertions of the hAC6 sequence shall be construed as affecting homology.

Thus, the claimed hAC6 polypeptide that is the subject of this invention includes molecules having the hAC6 amino acid sequence; fragments thereof having a consecutive sequence of at least 10, 15, 20, 25, 30 or 40 amino acid residues from the hAC6 sequence of FIG. 1, which exhibits the hAC6 polypeptide characteristics; amino acid sequence variants of the hAC6 sequence of FIG. 1 wherein an amino acid residue has been inserted N- or C-terminal to, or within, (including parallel deletions) the hAC6 sequence or its fragments as defined above; amino acid sequence variants of the hAC6 sequence of FIG. 1 or its fragments as defined above which have been substituted by at least one residue, and which exhibit the hAC6 polypeptide characteristics. Of particular interest are those peptides corresponding to those regions where the hAC6 polypeptide is divergent from types I–V and VII–IX.

Human type VI adenylyl cyclase polypeptides include those containing predetermined mutations by, e.g., homologous recombination, site-directed or PCR mutagenesis; naturally occurring variants of the hAC6 polypeptide; derivatives of the hAC6 polypeptide or its fragments wherein the hAC6 or its fragments have been covalently modified by substitution, chemical, enzymatic, or other appropriate means with a moiety other than a naturally occurring amino acid (for example a detectable moiety such as an enzyme or radioisotope); glycosylation variants of the hAC6 (insertion of a glycosylation site or deletion of any glycosylation site by deletion, insertion or substitution of appropriate amino acid); and soluble forms of the hAC6 polypeptide or fragments thereof. This invention also includes tagging the hAC6 polypeptide, for example, for use in a diagnostic application. Types and methods of tagging are well known in the art, for example, the use of hexa-histidine tags.

Several regions of the Type VI isoform are highly conserved with the other adenylyl cyclase isoforms. Accordingly, it is believed that most sequence modifications to the highly conserved regions such as the extracellular domains, transmembrane regions and short intracellular domains, including deletions and insertions, and substitutions in particular, are not expected to produce radical changes in the characteristics of the hAC6 polypeptide, distinct from those found with similar changes to other isoforms. However, when it is difficult to predict the exact effect of the sequence modification in advance of making the change, one skilled in the art will appreciate that the effect of any sequence modification will be evaluated by routine screening assays.

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal $H^+_2$ and C-terminal $O^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity. All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6 carbons.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH═CH—(cis and trans), —COCH$_2$—, —CH(OH)CH$_2$—and —CH$_2$ SO—. This replacement can be made by methods known in the art. The following references describe preparation of peptide analogs which include these alternative-linking moieties: Spatola, *Vega Data* 1(3) "Peptide Backbone Modifications" (general review) (March 1983); Spatola, in "Chemistry and Biochemistry of Amino Acids Peptides and Proteins," B. Weinstein, eds., Marcel Dekker, New York, p. 267 (1983) (general review); Morley, J. S., *Trends Pharm Sci*, pp. 463–468 (general review) (1980); Hudson, et al., *Int J Pept Prot Res* 14: 177–185 (—CH$_2$NH—, —CH$_2$CH$_2$—) (1979); Spatola, et al., *Life Sci* 38:1243–1249 (—CH$_2$—S) (1986); Hann, *J Chem Soc Perkin Trans I* 307–314 (—CH—CH—, cis and trans) (1982); Almquist, et al., *J Med Chem* 23:1392–1398 (—COCH$_2$—) (1980); Jennings-White, et al., *Tetrahedron Lett* 23:2533 (—COCH$_2$—) (1982); Szelke, et al., European Application EP 45665 (1982) CA:97:39405 (1982) (—CH (OH)CH$_2$—); Holladay, et al., *Tetrahedron Lett* 4: 4401–4404 (—C(OH)CH$_2$—) (1983); and Hruby, *Life Sci* 31:189–199 (—CH$_2$—S—) (1982).

Human type VI adenylyl cyclase peptides may be purified using techniques of classical protein chemistry, such as are well known in the art. For example, a lectin affinity chromatography step may be used, followed by a highly specific ligand affinity chromatography procedure that utilizes a ligand conjugated to biotin through the cysteine residues of the ligand. Alternately, the hexa-histidine tagged hAC6 polypeptide may be purified using nickel column chromatography.

One embodiment of the invention relates to recombinant materials associated with the production of the hAC6 polypeptide. One method of producing hAC6 comprises incorporating a nucleic acid having the nucleotide sequence of FIG. 1 (SEQ ID NO:1) into an expression vector, transforming a host cell with the vector and culturing the transformed host cell under conditions which result in expression of the gene. Suitable expression vectors include pc3hAC6. Examples of host cells includes bacterial, viral, yeast, insect or mammalian cell lines. A preferred host cell is the human embryonic cell line referred to as "HEK-293".

The invention also contemplates the use of transfected cells that can be cultured so as to display or express hAC6 on its surface, thus providing an assay system for the interaction of materials with the native hAC6 where these cells or relevant fragments of hAC6 are used as a screening tool to evaluate the effect of various candidate compounds on hAC6 activity in vivo, as is described below. Another embodiment of the invention relates to recombinant materials associated with the production of soluble hAC6 fragments. These include transfected cells, such as *E. coli*, that can be cultured so as to express active portions of the hAC6 polypeptide, in particular the C1 and C2 (C-terminus) intracellular loops. These soluble fragments can be purified and reconstituted to obtain enzymatic activity. This has been demonstrated with like domains from other isoforms. See Whisnant, et al., *Proc. Natl. Acad. Sci.*: 93:6621–6625 (1996). Such soluble fragments can also be used as a screening tool to evaluate the effect of various candidate compounds on hAC6 activity. Suitable cells for transfection include bacterial cells, insect cells such as Sf-9 cells, yeast cells and most mammalian cell lines.

Recombinant production of the hAC6 polypeptide involves using a nucleic acid sequence that encodes hAC6, as is set forth in FIG. 1, or its degenerate analogs. The nucleic acid can be prepared either by retrieving the native sequence, as described below, or by using substantial portions of the known native sequence as a probe, or it can be synthesized de novo using procedures that are well known in the art.

The nucleic acid may be ligated into expression vectors suitable for the desired host and then transformed into compatible cells. Suitable vectors suitable for use in transforming bacterial cells are well known in the art. Plasmids and bacteriophages, such as lambda phage, are commonly used as vectors for bacterial hosts such as *E. coli*. Virus vectors are suitable for use in mammalian and insect cells for expression of exogenous DNA. Mammalian cells are readily transformed with SV40 or polyoma virus; and insect cells in culture may be transformed with baculovirus expression vectors. Suitable yeast vector systems include yeast centromere plasmids, yeast episomal plasmids and yeast integrating plasmids. Alternatively, nucleic acids may be introduced directly into a host cell by techniques such as are well known in the art.

The cells are cultured under conditions favorable for the expression of the gene encoding the hAC6 polypeptide and cells displaying hAC6 on the surface are then harvested. Suitable eukaryotic host cells include mammalian cells, plant cells, yeast cells and insect cells. Suitable prokaryotic host cells, include bacterial cells such as *E. coli* and *Bacillus subtilis*, Chinese Hamster Ovary cells, COS cells, the rat-2 fibroblast cell line, the human embryonic kidney 293 cell line, and insect cell lines such as Sf-9.

This invention also relates to nucleic acids that encode or are complementary to a hAC6 polypeptide. These nucleic acids can then be used to produce the polypeptide in recombinant cell culture for diagnostic use or for potential therapeutic use. In still other aspects, the invention provides an isolated nucleic acid molecule encoding hAC6, either labeled or unlabeled, or a nucleic acid sequence that is complementary to, or hybridizes under stringent conditions to, a nucleic acid sequence encoding hAC6. The isolated nucleic acid molecule of the invention excludes nucleic acid sequences which encode, or are complementary to nucleic acid sequences encoding, other known adenylyl cyclase isoforms.

This invention also provides a replicable vector comprising a nucleic acid molecule encoding hAC6 operably linked to control sequences recognized by a host transformed by the vector; host cells transformed with the vector; and a method of using a nucleic acid molecule encoding hAC6 to effect the production of hAC6 on the cell surface or as soluble fragments, comprising expressing the nucleic acid molecule in a culture of the transformed host cells and recovered from the cells. The nucleic acid sequence is also useful in hybridization assays for hAC6-encoding nucleic acid molecules.

In still further embodiments of the invention, a method is described for producing hAC6 comprising inserting into the DNA of a cell containing the nucleic acid sequence encoding hAC6, a transcription modulatory element (such as an enhancer or a silencer) in sufficient proximity and orientation to the hAC6-coding sequence to influence transcription thereof, with an optional further step comprising culturing the cell containing the transcription modulatory element and the hAC6-encoding nucleic acid sequence.

This invention also covers a cell comprising a nucleic acid sequence encoding the hAC6 polypeptide and an exogenous transcription modulatory element in sufficient proximity and orientation to the above coding sequence to influence transcription thereof and a host cell containing the nucleic acid sequence encoding hAC6 operably linked to exogenous control sequences recognized by the host cell.

This invention provides a method for obtaining cells having increased or decreased transcription of the nucleic acid molecule encoding the hAC6 polypeptide, comprising: providing cells containing the nucleic acid molecule; introducing into the cells a transcription modulating element; and screening the cells for a cell in which the transcription of the nucleic acid molecule is increased or decreased.

Human adenylyl cyclase type VI nucleic acids for use in the invention can be produced as follows. A hAC6 "nucleic acid" is defined as RNA or DNA that encodes the hAC6 polypeptide, or is complementary to nucleic acid sequence encoding hAC6, or hybridizes to such nucleic acid and remains stably bound to it under stringent conditions, or encodes a polypeptide sharing at least 75% sequence identity, preferably at least 80%, and more preferably at least 85%, with the deduced amino acid sequence shown in FIG. 1. It is typically at least about 10 nucleotides in length and preferably has hAC6 related biological or immunological activity. Specifically contemplated are genomic DNA, cDNA, mRNA and antisense molecules, as well as nucleic acids based on alternative backbone or including alternative bases whether derived from natural sources or synthesized.

Of particular interest is a hAC6 nucleic acid that encodes a full-length molecule, including but not necessarily the native signal sequence thereof. Nucleic acid encoding full-length protein is obtained by screening selected cDNA or genomic libraries using the deduced amino acid sequence disclosed herein for the first time, and, if necessary, using conventional primer extension procedures to secure DNA that is complete at its 5' coding end. Such a clone is readily identified by the presence of a start codon in reading frame with the original sequence.

DNA encoding an amino acid sequence variant of the hAC6 polypeptide is prepared as described below or by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of hAC6.

Techniques for isolating and manipulating nucleic acids are disclosed for example by the following documents: U.S. Pat. No. 5,030,576, U.S. Pat. No. 5,030,576 and International Patent Publications WO94/11504 and WO93/03162. See, also, Sambrook, et al., "Molecular Cloning: A Laboratory Manual", 2nd Edition, Cold Spring Harbor Press, Cold Spring Harbor, N.Y., 1989, and Ausubel, et al. "Current Protocols in Molecular Biology", Vol. 2, Wiley-Interscience, New York, 1987. The isolation, recombinant production and characterization of the hAC6 polypeptide allows for the design of assay systems using hAC6. The availability of the isolated cells providing hAC6 on their surface and the availability of the recombinant DNA encoding hAC6 which permits display and expression of the enzyme on host cell surfaces, all makes such cells available as a valuable tool for evaluating the ability of candidate pharmaceuticals, both agonists and antagonists, to affect the activity of hAC6. In this manner, the invention is related to assay systems which utilize isolated or recombinantly produced hAC6 to screen for agonist and antagonist activity of candidate drugs. This assay is especially useful in assuring that these candidate therapeutic agents have the desired effect on hAC6. Determination of these properties is essential in evaluating the specificity of drugs for other adenylyl cyclase isoforms.

The host cells are typically animal cells, most typically mammalian cells. In order to be useful in the assays, the cells must have intracellular mechanisms which permit hAC6 to be displayed on the cell surface or to be expressed as soluble fragments. The animal host cells expressing the DNA encoding the hAC6 polypeptide or a fragment thereof are then cultured to effect the expression of the encoding nucleic acids so as to either 1) produce hAC6 display on the cell surface such that the cells can then be used directly in assays for assessment of a candidate drug to bind to or otherwise affect the activity of the enzyme, or 2) produce hAC6 as soluble fragments which can then be purified and reconstituted to obtain an enzymatically active compound useful in screening assays.

There are several possible strategies to identify compounds which affect hAC6 activity. Over expression of the hAC6 cDNA can provide a means for isolation of large quantities of crude membrane preparations from a stable cell line. HEK-293 cells have been found to be particularly useful for this purpose. In this system the measurable enzyme activity would be predominantly from expression of recombinant hAC6. A highly sensitive, reproducible, high throughput screening system is desirable, with enzyme activity detected in a 96 well, scintillation proximity-type assay to measure product formation (cAMP). There are numerous screening assays that can be utilized. For example, the basal (unstimulated) activity of hAC6 can be measured as a method of detecting both agonists and antagonists of the hAC6 enzyme. In addition, stimulation of the enzyme by its most relevant physiological activator, the heterotrimeric G protein subunit, $G_{\alpha s}$, can be assayed using activated (GTPγS bound) recombinant bovine $G_{\alpha s}$ (expressed and purified from bacteria), with the expectation that additional compounds may be identified which inhibit $G_{\alpha s}$ stimulation of the hAC6 polypeptide. Other stimulatory agents can also be used, such as forskolin or forskolin analogs. "Hits", i.e., compounds which affect hAC6, in any of these screens will be further evaluated in other assays to help focus on compounds which are relevant to the targeted isoform.

Another method of evaluating candidates as potential therapeutic agents typically involves a screening based approach such as a binding assay in which the candidate (such as a peptide or a small organic molecule) would be tested to measure if, or to what extent, it binds the catalytic subunit of the hAC6 enzyme. Preferably, a mammalian cell line that expresses recombinant hAC6 or plasma membrane preparations thereof, will be used in the assay. For example, a candidate antagonist competes for binding to hAC6 with either a labeled agonist or antagonist, for example labeled forskolin or a labeled forskolin analog. Varying concentrations of the candidate are supplied, along with a constant concentration of the labeled agonist or antagonist. The inhibition of binding of the labeled material can then be measured using established techniques. This measurement is then correlated to determine the amount and potency of the candidate that is bound to hAC6.

Another method of identifying compounds which affect hAC6 activity is the rational design of synthetic compounds based on nucleotide scaffolds, targeted to either of two distinct sites on the hAC6 enzyme. One of these is the active site (ATP being the substrate, cAMP being the product) and the other is the separate P site (adenine nucleoside 3'-polyphosphates reportedly demonstrating the greatest inhibitory activity, with either pure or crude enzyme preparations). As a related approach, one could attempt to design forskolin analogues which may demonstrate isoform specific effects.

In addition, using the above assays, the ability of a candidate drug to stimulate or inhibit the activity of hAC6 can be tested directly.

Once lead candidates are identified, and for purposes of demonstrating that isoform specificity may be achieved with small molecule modulators, it is desirable to develop assay systems which monitor most, and preferably all, human adenylyl cyclase isoforms. These assays may be used to evaluate either existing (e.g. forskolin analogs or P site inhibitors) or newly discovered small molecule modulators and determine structure activity relationships for different adenylyl cyclase isoforms. Such assays could also be used to evaluate either specific or selective modulators of other adenylyl targets and with use of a whole cell assay, may provide useful insights for designing bioavailability and addressing biological activity of lead candidates.

The hAC6 also has utility in assays for the diagnosis of diseases and disorders by detection, in tissue samples, of aberrant expression of the hAC6 enzyme.

Another aspect of the invention relates to hAC6 agonists that imitate the naturally occurring form of hAC6. These agonists are useful as control reagents in the above-mentioned assays to verify the workability of the assay system. In addition, agonists for hAC6 may exhibit useful effects in vivo in treating disease.

Another aspect of the invention relates to hAC6 antagonists that are modified forms of hAC6 peptides. Such antagonists bind to hAC6, and prevent enzyme-substrate interaction by blocking their binding to hAC6. Another group of compounds within the scope of the invention, are antagonists of hAC6 substrate, i.e., these are substrate inhibitors. Both these types of antagonists find utility in diminishing or mediating events based upon enzyme-substrate interaction such as cAMP production. Yet another second group of antagonists includes antibodies designed to bind specific portions of hAC6. In general, these are monoclonal antibody preparations which are highly specific for any desired region of hAC6, although polyclonal antibodies are also contemplated by this invention. The antibodies, which are explained in greater detail below, are also useful in immunoassays for the hAC6 enzyme, for example, in assessing successful expression of the gene in recombinant systems.

In both the agonists and antagonists, a preferred embodiment is that class of compounds having amino acid sequences that are encoded by the hAC6 gene. The invention also includes those compounds where one, two, three or more of said amino acid residues are replaced by one(s) which is not encoded genetically. Also included in the invention are isolated DNA molecules that encode these specific peptides.

It is believed that the extracellular domains of enzymes may play a key role in extracellular activities, for example, in enzyme regulation. Accordingly, the invention includes agonists and antagonists having amino acid sequences, in whole or in part, corresponding to the extracellular domains of hAC6, the sequences of which can be approximated from the amino acid sequence of FIG. 1 and the hydropathy analysis of FIG. 4. The invention also includes agonists and antagonists that affect the enzyme's function by binding to the N- or C-terminus or to one of the intracellular (ICD) domains of hAC6, the sequences of which can be approximated from the amino acid sequence of FIG. 1 and the hydropathy analysis.

In other adenylyl cyclases, the ICD IV and carboxy terminus regions have been shown to play a role in enzyme activity or $G_\alpha$ or forskolin interaction. See for example: Whisnant, et al., supra. Accordingly, it is expected that the amino acid sequences of the ICD IV and carboxy terminus regions of hAC6, in whole or in part, will be particularly useful in designing antibodies or peptides that can bind the enzyme and block enzyme activity or $G_{\alpha s}$ interaction.

As the understanding of adenylyl cyclases and factors which effect isoform activity increases, rational drug design is becoming a viable alternative in pharmaceutical research. It is believed that the two conserved intracellular domains of adenylyl cyclase (the $C_1$ and $C_2$ domains) associate to form an active enzyme. This has been demonstrated with studies that combine both expressed recombinant $C_1$ and $C_2$ domains. Both the $C_1$ and $C_2$ domains are required to reconstitute enzyme activity while either alone has no substantial activity. Forskolin plus $G_{\alpha s}$ stimulates this system, by increasing the association of the two domains. Designing assays which monitor enzyme activity, dependent on association of two separate domains, is expected to provide greater sensitivity to antagonists since this would presumably be more easily disrupted. Other studies have demonstrated that peptides, comprised of sequences from conserved regions of the intracellular domains, act as inhibitors of detergent solubilized enzyme preparations. This invention contemplates the use of peptide walking strategies, to delimit regions of the modulator which may be responsible for its activity, leading to the design of small molecule inhibitors. Finally, knowledge of uncharacterized, physiological modulators of adenylyl cyclase, particularly those that demonstrate isoform specificity, may provide new assay systems for identifying novel AC modulators. It is expected that many of these modulators would be proteins and some may be identified while using adenylyl cyclase sequences as "bait" in a yeast two hybrid system. Alternatively one may identify proteins which coprecipitate with adenylyl cyclase upon capture with adenylyl cyclase antibodies.

The peptide agonists and antagonists of the invention are preferably about 10–100 amino acids in length, more preferably 25–75 amino acids in length. These peptides can be readily prepared using standard solid phase or solution phase peptide synthesis, as is well known in the art. In addition, the DNA encoding these peptides can be synthesized using commercially available oligonucleotide synthesis instrumentation and recombinantly produced using standard recombinant production systems. Production using solid phase peptide synthesis is required when non-gene encoded amino acids are to be included in the peptide.

Another aspect of the invention pertains to antibodies, which have both diagnostic and therapeutic uses. Antibodies are able to act as antagonists or agonists by binding specific regions of the hAC6 polypeptide. These antibodies also find utility in immunoassays that measure the presence of hAC6, for example in immunoassays that measure gene expression. In general, antibodies to adenylyl cyclases, and more importantly, those which may recognize specific isoforms of adenylyl cyclase, are a useful tool to evaluate tissue distribution and prevalence of the adenylyl cyclase protein. By identifying regions of dissimilarity between the adenylyl cyclase isoforms and the antigenic potential of these regions, either synthetic peptides or recombinant proteins to these sequences can be created for use in immunization. The resulting antibodies would then be characterized for specificity based on the unique qualities of the immunogen and reactivity with other expressed isoforms. Detection of isoform protein in various tissues can readily be monitored by Westerns blots; however, immunohistochemical analysis would also be useful. This information is useful to identify the adenylyl cyclase target of interest, providing valuable insights into useful therapeutic strategies such as targets in cardiovascular disease, asthma or obesity.

The antibodies of the present invention can be prepared by techniques that are well known in the art. The antibodies can be monoclonal or polyclonal, but are preferably monoclonal antibodies that are highly specific for hAC6 and can be raised against the whole hAC6 polypeptide or regions thereof. Antibodies are prepared by immunizing suitable mammalian hosts (typically rabbit, rat, mouse, goat, human, etc.) in appropriate immunization protocols using the peptide haptens (immunogen) alone, if they are of sufficient length, or, if desired, or if required to enhance immunogenicity, conjugated to suitable carriers. The immunogen will typically contain a portion of the hAC6 polypeptide that is intended to be targeted by the antibodies. Critical regions include those regions corresponding to the extracellular domains of the hAC6 enzyme, any region(s) of proteolytic cleavage, and any segment(s) of the extracellular segment critical for activation. Methods for preparing immunogenic conjugates with carriers such as bovine serum albumin, keyhole limpet hemocyanin, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten can be extended at the amino or carboxy terminus with a cysteine residue or interspersed with cysteine residues, for example, to facilitate linking to carrier. The desired immunogen is administered to a host by injection over a suitable period of time using suitable adjuvants followed by collection of sera. Over the course of the immunization schedule, titers of antibodies are taken to determine the adequacy of antibody formation.

Polyclonal antibodies are suitable for many diagnostic and research purposes and are easily prepared. Monoclonal antibodies are often preferred for therapeutic applications and are prepared by continuous hybrid cell lines and collection of the secreted protein. Immortalized cell lines that secrete the desired monoclonal antibodies can be prepared by the method described in Kohler and Milstein, *Nature* 256:495–497 (1975) or modifications which effect immortalization of lymphocytes or spleen cells, as is generally known. The immortalized cell lines are then screened by immunoassay techniques in which the antigen is the immunogen or a cell expressing hAC6 on its surface. Cells that are found to secrete the desired antibody, can then be cultured in vitro or by production in the ascites fluid. The antibodies are then recovered from the culture supernatant or from the ascites supernatant.

Alternately, antibodies can be prepared by recombinant means, i.e., the cloning and expression of nucleotide sequences or mutagenized versions thereof that at a minimum code for the amino acid sequences required for specific binding of natural antibodies. Antibody regions that bind specifically to the desired regions of hAC6 can also be produced as chimeras with regions of multiple species origin.

Antibodies may include a complete immunoglobulin or a fragment thereof, and includes the various classes and isotypes such as IgA, IgD, IgE, IgG1, IgG2a, IgG2b, IgG3 and IgM. Fragments include Fab, Fv, F(ab')$_2$, Fab', and so forth. Fragments of the monoclonals or the polyclonal antisera which contain the immunologically significant portion can be used as antagonists, as well as the intact antibodies. Use of immunologically reactive fragments, such as the Fab, Fab', or F(ab')$_2$ fragments is often preferable, especially in a therapeutic context, as these fragments have different immunogenicity than the whole immunoglobulin, and do not carry the biological activity of an immunoglobulin constant domain.

The antibodies thus produced are useful not only as potential agonist or antagonists for the hAC6 polypeptide, filling the role of agonist or antagonist in the assays of the invention, but are also useful in immunoassays for detecting the hAC6 enzyme. As such these antibodies can be coupled to imaging agents for administration to a subject to allow detection of localized antibody to ascertain the under-or over-expression of hAC6 in tissues of interest. In addition, these reagents are useful in vitro to detect, for example, the successful production of hAC6 on the surface of the recombinant host cells.

Yet another aspect of the invention relates to pharmaceutical compositions containing the compounds and antibodies of the invention. The agonists and antagonists of the invention have therapeutic utility in (1) treating diseases caused by aberrant activity of the hAC6 enzyme in tissues where it is customarily found, for example in the heart and brain and (2) treating diseases whose symptoms can be ameliorated by stimulating or inhibiting the activity of hAC6.

The peptide agonists and antagonists of the invention can be administered in conventional formulations for systemic administration such as is well known in the art. Typical formulations may be found, for example, in *Remington's Pharmaceutical Sciences*, Mack Publishing Co., Easton Pa., latest edition.

Preferred forms of systemic administration include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1–100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

The invention also relates to the therapeutic, prophylactic and research uses of various techniques to block or modulate the expression of the hAC6 by interfering with the transcription of translation of a DNA or RNA molecule encoding the hAC6. This includes a method to inhibit or regulate expression of hAC6 in a cell comprising providing to the cell an oligonucleotide molecule which is antisense to, or forms a triple helix with, hAC6-encoding DNA or with DNA regulating expression of hAC6-encoding DNA, in an amount sufficient to inhibit or regulate expression of the hAC6, thereby inhibiting or regulating its expression. Also included is a method to inhibit or regulate expression of hAC6 in a subject, comprising administering to the subject an oligonucleotide molecule which is antisense to, or forms a triple helix with, hAC6-encoding DNA or with DNA regulating expression of hAC6-encoding DNA, in an amount sufficient to inhibit or regulate expression of hAC6 in the subject, thereby inhibiting or regulating its expression. The antisense molecule or triple helix-forming molecule in the above methods is preferably a DNA or RNA oligonucleotide. These utilities are described in greater detail below.

The constitutive expression of antisense RNA in cells has been shown to inhibit the expression of about 20 different genes in mammals and plants, and the list continually grows (Hambor, et al., *J. Exp. Med.* 168:1237–1245 (1988); Holt, et al., *Proc. Natl. Acad. Sci.* 83:4794–4798 (1986); Izant, et al., *Cell* 36:1007–1015 (1984); Izant, et al., *Science* 229: 345–352 (1985) and De Benedetti, et al., *Proc. Natl. Acad. Sci.* 84:658–662 (1987)). Possible mechanisms for the antisense effect are the blockage of translation or prevention of splicing, both of which have been observed in vitro. Interference with splicing allows the use of intron sequences (Munroe, *EMBO. J.* 7:2523–2532 (1988) which should be less conserved and therefore result in greater specificity in inhibiting expression of a protein of one species but not its homologue in another species.

Therapeutic gene regulation is accomplished using the "antisense" approach, in which the function of a target gene in a cell or organism is blocked, by transfection of DNA, preferably an oligonucleotide, encoding antisense RNA which acts specifically to inhibit expression of the particular target gene. The sequence of the antisense DNA is designed to result in a full or preferably partial antisense RNA transcript which is substantially complementary to a segment of the gene or mRNA which it is intended to inhibit. The complementarity must be sufficient so that the antisense RNA can hybridize to the target gene (or mRNA) and inhibit the target gene's function, regardless of whether the action is at the level of splicing, transcription or translation. The degree of inhibition, readily discernible by one of ordinary skill in the art without undue experimentation, must be sufficient to inhibit, or render the cell incapable of expressing, the target gene. One of ordinary skill in the art will recognize that the antisense RNA approach is but one of a number of known mechanisms which can be employed to block specific gene expression.

By the term "antisense" is intended an RNA sequence, as well as a DNA sequence coding therefor, which is sufficiently complementary to a particular mRNA molecule for which the antisense RNA is specific to cause molecular hybridization between the antisense RNA and the mRNA such that translation of the mRNA is inhibited. Such hybridization must occur under in vivo conditions, that is, inside the cell. The action of the antisense RNA results in specific inhibition of gene expression in the cell. See Albers, et al., "Molecular Biology Of The Cell", 2nd Ed., Garland Publishing, Inc., New York, N.Y. (1989), in particular, pages 195–196.

The antisense RNA of the present invention may be hybridizable to any of several portions of a target mRNA, including the coding sequence, a 3' or 5' untranslated region, or other intronic sequences. A preferred antisense RNA is that complementary to hAC6 mRNA. As is readily discernible by one of skill in the art, the minimal amount of homology required by the present invention is that sufficient to result in hybridization to the specific target mRNA and inhibition of its translation or function while not affecting function of other mRNA molecules and the expression of other genes.

Antisense RNA is delivered to a cell by transformation or transfection with a vector into which has been placed DNA encoding the antisense RNA with the appropriate regulatory sequences, including a promoter, to result in expression of the antisense RNA in a host cell.

"Triple helix" or "triplex" approaches involve production of synthetic oligonucleotides which bind to the major groove of a duplex DNA to form a colinear triplex. Such triplex formation can regulate and inhibit cellular growth. See, for example, Hogan, et al., U.S. Pat. No. 5,176,996; Cohen, et al., *Sci. Amer., December* 1994, p. 76–82; Helene, *Anticancer Drug Design* 6:569–584 (1991); Maher III, et al., *Antisense Res. Devel.* 1:227–281 (Fall 1991); and Crook, et al. eds., "Antisense Research and Applications", CRC Press, 1993; all of which are incorporated herein by reference. It is based in part on the discovery that a DNA oligonucleotide can bind by triplex formation to a duplex DNA target in a gene regulatory region, thereby repressing transcription initiation (Cooney, et. al. *Science* 241:456 (1988)). The present invention utilizes methods such as those of Hogan et al., supra, to designing oligonucleotides which will bind tightly and specifically to a duplex DNA target comprising part of the hAC6-encoding DNA or a regulatory sequence thereof. Such triplex oligonucleotides can therefore be used as a class of drug molecules to selectively manipulate the expression of this gene.

Thus the present invention is directed to providing to a cell or administering to a subject a synthetic oligonucleotide in sufficient quantity for cellular uptake and binding to a DNA duplex of the target hAC6-coding DNA sequence or a regulatory sequence thereof, such that the oligonucleotide binds to the DNA duplex to form a colinear triplex. This method is used to inhibit expression of the hAC6 enzyme on cells in vitro or in vivo. Preferably the target sequence is positioned within the DNA domain adjacent to the RNA transcription origin. This method can also be used to inhibit growth of cells which is dependent on expression of this enzyme. The method may also be used to alter the relative amounts or proportions of the hAC6 expressed on cells or tissues by administering such a triplex-forming synthetic oligonucleotide.

The following examples are intended to illustrate but not to limit the invention.

EXAMPLE 1

Construction and Screening of a Human Heart cDNA Library

Whole human heart was used as a source of mRNA. The libraries were purchased from a commercial source, Clontech (Catalog No. HL3026a). The libraries were prepared in a lambda gt10 phage with both oligo-dT and random primers. The primary screening of the lambda gt10 library was carried out with gentle washing (less stringent conditions). Prehybridization and hybridization were carried out at standard conditions. A suitable PCR AC fragment was used as a probe.

The probe was radiolabeled with $^{32}$P-dCTP by the random primer labeling method. After hybridization, the blot was washed under increasingly stringent conditions and then radioautographed. A positive clone was obtained.

The next step was to ascertain the full length cDNA sequence from the inserts in the clones. All the positive clones from the human heart library were subcloned into a suitable plasmid. After restriction maps were made, they were further subcloned and sequenced with universal primers or synthesized oligomers. The sequence was performed bidirectionally with Sequenase (Tabor, et al., *Proc. Natl. Acad. Sci. USA* 84:4767–4771 (1987).

Clone were either used on their own, or sequenced and then used to generate PCR primers which were used to acquire additional clones of interest, by the PCR-based RACE ("rapid amplification of cDNA ends") technique (Frohman, M. A., *Methods Enzymol.* 218:340–362 (1991)) and human heart mRNA. One clone of particular interest was used as a probe to screen a separate human heart library and several more clones were obtained. Sequencing revealed an open reading frame of 3504 bases reads through to a TGA, a translation termination codon (FIG. 1). Thus, the clone(s) encode a protein of 1168 amino acids. The entire coding portion of the cDNA and its deduced amino acid sequence are shown (FIG. 1) (SEQ ID NO: 1 and 2, respectively).

One or more fragments from these clones were subcloned into pcDNA3, obtained from Invitrogen. The resulting expression vector, containing the full length cDNA, was given a designation. Samples of this expression vector, inserted into an appropriate *E. coli* strain designated SURE, were deposited with the American Type Culture Collection, 10801 University Boulevard. Manassas. Va. 20110. on Mar. 5, 2002 in accordance with the Budapest Treaty on the International Recognition of the Deposit of Microorganisms for the Purposes of Patent Procedure and have been accorded accession number ATCC PTA-4118.

EXAMPLE 2

Cloning and Expression of the Human Type VI Adenylyl Cyclase

The human type VI adenylyl cyclase was produced by cloning and expressing heart type VI adenylyl cyclase cDNA in a suitable expression system using recombinant DNA methods, such as are well known in the art.

Purified plasmid was transfected into HEK-293 cells using electroporation. The cells were grown in an appropriate growth medium then washed. After the addition of trypsin solution, the cells were incubated, harvested and resuspended in the growth media. Purified plasmid was added to an electroporation cuvette. Cells were added to the DNA and the mixture was pulsed. The cell-DNA mixture was then plated into a suitable growth media. The plate was incubated before placing cells on a suitable selective media.

hAC6, having 1168 amino acids, was analyzed for secondary structure by the method of Kyte, et al., *J. Mol. Biol.* 157:105–132 (1982). The software, GeneWorks; v. 2.45; IntelliGenetics, Inc.; Mountain View; Calif. was used to obtain a hydropathy plot, and thereby identify the membrane related structure of this adenylyl cyclase isoform. The method of Kyte, et al., supra, was used with a window size of 5.

Twelve peaks appear in the hydropathy plot, not shown, which represent transmembrane spanning regions. These results suggest that this adenylyl cyclase isoform has a structure of twelve transmembrane spanning regions, as well as a large cytoplasmic loop located in the middle and at the end, which is consistent with the structures of the previously characterized isoforms.

EXAMPLE 3

Evaluation of the Human Type VI Adenylyl Cyclase

The biochemical characteristics of hAC9 were determined in a stable expression system using HEK-293 cells. A fragment of the adenylyl cyclase cDNA containing the whole coding sequence was inserted into a suitable plasmid.

An assay was performed to measure cAMP product formation and it was determined that the hAC6 enzyme expressed by this cDNA was active.

EXAMPLE 4

Tissue Distribution of the Human Type VI Adenylyl Cyclase

In order to determine the tissue distribution of hAC6, Northern blotting was performed using mRNA from various tissues. Messenger RNA was purified using guanidium sodium and oligo-dT columns from various human tissues.

The blot was pre-hybridized in a suitable solution before the addition of a probe. Hybridization was performed, followed by washing under increasingly stringent conditions. The blot was then autoradiographed.

The results of the Northern blot analysis indicated that hAC6 is predominantly expressed in heart and brain tissue, although some expression was also found at slight levels in other tissues.

All references cited and mentioned above, including patents, journal articles and texts, are all incorporated by reference herein, whether expressly incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for identifying a candidate compound which binds to a polypeptide selected from the group consisting of:
   a) a polypeptide comprising the amino acid sequence of SEQ ID NO:2;
   b) a polypeptide encoded by the nucleotide sequence set forth in SEQ ID NO:1; and
   c) a polypeptide encoded by nucleotides 145–3648 of the nucleotide sequence set forth in SEQ ID NO:1;
   the method comprising:
   i) contacting a sample comprising the polypeptide with a test compound under conditions suitable for binding; and
   ii) detecting binding of the test compound to the polypeptide; thereby identifying a compound which binds to the polypeptide.

2. The method of claim 1, wherein the polypeptide further comprises an amino acid sequence tag.

3. The method of claim 2, wherein the tag is a histidine tag.

4. The method of claim 1, wherein the sample is an isolated polypeptide, a membrane-bound form of an isolated polypeptide or a cell comprising the polypeplide.

5. The method of claim 4, wherein the cell is a mammalian cell.

6. The method of claim 1, wherein the binding of the test compound to the polypeptide is detected by a method selected from the group consisting of:
   a) direct detection of test compound/polypeptide binding;
   b) a competition binding assay; and
   c) an immunoassay.

* * * * *

SEQUENCE LISTING

```
<160> NUMBER OF SEQ ID NOS: 2

<210> SEQ ID NO 1
<211> LENGTH: 4942
<212> TYPE: DNA
<213> ORGANISM: human type VI adenylyl cyclase
<220> FEATURE:
<221> NAME/KEY: CDS
<222> LOCATION: (145)..(3648)

<400> SEQUENCE: 1
gcggacggcg gacggcggac ggcgggcggg acggccagga cgcgcgggct cggaggaccg        60
cgggacggcc ggccggccgg ccggagcccg cggggggcggc ggggcggggg cccagggcag      120
gcgcggagcc gggccggcag caac atg tca tgg ttt agt ggc ctc ctg gtc         171
                          Met Ser Trp Phe Ser Gly Leu Leu Val
                            1               5 cct aaa gtg gat gaa cgg aaa aca gcc tgg ggt gaa cgc aat ggg cag        219
Pro Lys Val Asp Glu Arg Lys Thr Ala Trp Gly Glu Arg Asn Gly Gln
 10                  15                  20                  25 aag cgt tcg cgg cgc cgt ggc act cgg gca ggt ggc ttc tgc acg ccc        267
Lys Arg Ser Arg Arg Arg Gly Thr Arg Ala Gly Gly Phe Cys Thr Pro
                 30                  35                  40 cgc tat atg agc tgc ctc cgg gat gca gag cca ccc agc ccc acc cct        315
Arg Tyr Met Ser Cys Leu Arg Asp Ala Glu Pro Pro Ser Pro Thr Pro
             45                  50                  55 gcg ggc ccc cct cgg tgc ccc tgg cag gat gac gcc ttc atc cgg agg        363
Ala Gly Pro Pro Arg Cys Pro Trp Gln Asp Asp Ala Phe Ile Arg Arg
         60                  65                  70 ggc ggc cca ggc aag ggc aag gag ctg ggg ctg cgg gca gtg gcc ctg        411
Gly Gly Pro Gly Lys Gly Lys Glu Leu Gly Leu Arg Ala Val Ala Leu
     75                  80                  85 ggc ttc gag gat acc gag gtg aca acg aca gcg ggc ggg acg gct gag        459
Gly Phe Glu Asp Thr Glu Val Thr Thr Thr Ala Gly Gly Thr Ala Glu
 90                  95                 100                 105 gtg gcg ccc gac gcg gtg ccc agg agt ggg aga tcc tgc tgg cgc cgt        507
Val Ala Pro Asp Ala Val Pro Arg Ser Gly Arg Ser Cys Trp Arg Arg
                110                 115                 120 ctg gtg cag gtg ttc cag tcg aag cag ttc cgt tcg gcc aag ctg gag        555
Leu Val Gln Val Phe Gln Ser Lys Gln Phe Arg Ser Ala Lys Leu Glu
            125                 130                 135 cac ctg tac cag cgg tac ttc ttc cag atg aac cag agc agc ctg acg        603
His Leu Tyr Gln Arg Tyr Phe Phe Gln Met Asn Gln Ser Ser Leu Thr
        140                 145                 150 ctg ctg atg gcg gtg ctg gtg ctc ctc aca gcg gtg ctg ctg gct ttc        651
Leu Leu Met Ala Val Leu Val Leu Leu Thr Ala Val Leu Leu Ala Phe
    155                 160                 165 cac gcc gca ccc gcc cgc cct cag cct gcc tat gtg gca ctg ttg gcc        699
His Ala Ala Pro Ala Arg Pro Gln Pro Ala Tyr Val Ala Leu Leu Ala
170                 175                 180                 185 tgt gcc gcc gcc ctg ttc gtg ggg ctc atg gtg gtg tgt aac cgg cat        747
```

```
Cys Ala Ala Ala Leu Phe Val Gly Leu Met Val Val Cys Asn Arg His
            190                 195                 200 agc ttc cgc cag gac tcc atg tgg gtg gtg agc tac gtg gtg ctg ggc    795
Ser Phe Arg Gln Asp Ser Met Trp Val Val Ser Tyr Val Val Leu Gly
        205                 210                 215 atc ctg gcg gca gtg cag gtc ggg ggc gct ctc gca gca gac ccg cgc    843
Ile Leu Ala Ala Val Gln Val Gly Gly Ala Leu Ala Ala Asp Pro Arg
            220                 225                 230 agc ccc tct gcg ggc ctc tgg tgc cct gtg ttc ttt gtc tac atc gcc    891
Ser Pro Ser Ala Gly Leu Trp Cys Pro Val Phe Phe Val Tyr Ile Ala
        235                 240                 245 tac acg ctc ctc ccc atc cgc atg cgg gct gcc gtc ctc agc ggc ctg    939
Tyr Thr Leu Leu Pro Ile Arg Met Arg Ala Ala Val Leu Ser Gly Leu
250                 255                 260                 265 ggc ctc tcc acc ttg cat ttg atc ttg gcc tgg caa ctt aac cgt ggt    987
Gly Leu Ser Thr Leu His Leu Ile Leu Ala Trp Gln Leu Asn Arg Gly
            270                 275                 280 gat gcc ttc ctc tgg aag cag ctc ggt gcc aat gtg ctg ctg ttc ctc   1035
Asp Ala Phe Leu Trp Lys Gln Leu Gly Ala Asn Val Leu Leu Phe Leu
        285                 290                 295 tgc acc aac gtc att ggc atc tgc aca cac tat cca gca gag gtg tct   1083
Cys Thr Asn Val Ile Gly Ile Cys Thr His Tyr Pro Ala Glu Val Ser
            300                 305                 310 cag cgc cag gcc ttt cag gag acc cgc ggt tac atc cag gcc cgg ctc   1131
Gln Arg Gln Ala Phe Gln Glu Thr Arg Gly Tyr Ile Gln Ala Arg Leu
        315                 320                 325 cac ctg cag cat gag aat cgg cag cag gag cgg ctg ctg ctg tcg gta   1179
His Leu Gln His Glu Asn Arg Gln Gln Glu Arg Leu Leu Leu Ser Val
330                 335                 340                 345 ttg ccc cag cac gtt gcc atg gag atg aaa gaa gac atc aac aca aaa   1227
Leu Pro Gln His Val Ala Met Glu Met Lys Glu Asp Ile Asn Thr Lys
            350                 355                 360 aaa gaa gac atg atg ttc cac aag atc tac ata cag aag cat gac aat   1275
Lys Glu Asp Met Met Phe His Lys Ile Tyr Ile Gln Lys His Asp Asn
        365                 370                 375 gtc agc atc ctg ttt gca gac att gag ggc ttc acc agc ctg gca tcc   1323
Val Ser Ile Leu Phe Ala Asp Ile Glu Gly Phe Thr Ser Leu Ala Ser
            380                 385                 390 cag tgc act gcg cag gag ctg gtc atg acc ctg aat gag ctc ttt gcc   1371
Gln Cys Thr Ala Gln Glu Leu Val Met Thr Leu Asn Glu Leu Phe Ala
        395                 400                 405 cgg ttt gac aag ctg gct gcg gag aat cac tgc ctg agg atc aag atc   1419
Arg Phe Asp Lys Leu Ala Ala Glu Asn His Cys Leu Arg Ile Lys Ile
410                 415                 420                 425 ttg ggg gac tgt tac tac tgt gtg tca ggg ctg ccg gag gcc cgg gcc   1467
Leu Gly Asp Cys Tyr Tyr Cys Val Ser Gly Leu Pro Glu Ala Arg Ala
            430                 435                 440 gac cat gcc cac tgc tgt gtg gag atg ggg gta gac atg att gag gcc   1515
Asp His Ala His Cys Cys Val Glu Met Gly Val Asp Met Ile Glu Ala
                445                 450                 455 atc tcg ctg gta cgt gag gtg aca ggt gtg aat gtg aac atg cgc gtg   1563
Ile Ser Leu Val Arg Glu Val Thr Gly Val Asn Val Asn Met Arg Val
        460                 465                 470 ggc atc cac agc ggg cgc gtg cac tgc ggc gtc ctt ggc ttg cgg aaa   1611
Gly Ile His Ser Gly Arg Val His Cys Gly Val Leu Gly Leu Arg Lys
            475                 480                 485 tgg cag ttc gat gtg tgg tcc aat gat gtg acc ctg gcc aac cac atg   1659
Trp Gln Phe Asp Val Trp Ser Asn Asp Val Thr Leu Ala Asn His Met
490                 495                 500                 505
```

```
                                                         -continued gag gca gga ggc cgg gct ggc cgc atc cac atc act cgg gca aca ctg       1707
Glu Ala Gly Gly Arg Ala Gly Arg Ile His Ile Thr Arg Ala Thr Leu
                510                 515                 520 cag tac ctg aac ggg gac tac gag gtg gag cca ggc cgt ggt ggc gag       1755
Gln Tyr Leu Asn Gly Asp Tyr Glu Val Glu Pro Gly Arg Gly Gly Glu
            525                 530                 535 cgc aac gcg tac ctc aag gag cag cac att gag act ttc ctc atc ctg       1803
Arg Asn Ala Tyr Leu Lys Glu Gln His Ile Glu Thr Phe Leu Ile Leu
        540                 545                 550 ggc gcc agc cag aaa cgg aaa gag gag aag gcc atg ctg gcc aag ctg       1851
Gly Ala Ser Gln Lys Arg Lys Glu Glu Lys Ala Met Leu Ala Lys Leu
    555                 560                 565 cag cgg act cgg gcc aac tcc atg gaa ggg ctg atg ccg cgc tgg gtt       1899
Gln Arg Thr Arg Ala Asn Ser Met Glu Gly Leu Met Pro Arg Trp Val
570                 575                 580                 585 cct gat cgt gcc ttc tcc cgg acc aag gac tcc aag gcc ttc cgc cag       1947
Pro Asp Arg Ala Phe Ser Arg Thr Lys Asp Ser Lys Ala Phe Arg Gln
                590                 595                 600 atg ggc att gat gat tcc agc aaa gac aac cgg ggc acc caa gat gcc       1995
Met Gly Ile Asp Asp Ser Ser Lys Asp Asn Arg Gly Thr Gln Asp Ala
            605                 610                 615 ctg aac cct gag gat gag gtg gat gag ttc ctg agc cgt gcc atc gat       2043
Leu Asn Pro Glu Asp Glu Val Asp Glu Phe Leu Ser Arg Ala Ile Asp
        620                 625                 630 gcc cgc agc att gat cag ctg cgg aag gac cat gtg cgc cgg ttt ctg       2091
Ala Arg Ser Ile Asp Gln Leu Arg Lys Asp His Val Arg Arg Phe Leu
    635                 640                 645 ctc acc ttc cag aga gag gat ctt gag aag aag tac tcc cgg aag gtg       2139
Leu Thr Phe Gln Arg Glu Asp Leu Glu Lys Lys Tyr Ser Arg Lys Val
650                 655                 660                 665 gat ccc cgc ttc gga gcc tac gtt gcc tgt gcc ctg ttg gtc ttc tgc       2187
Asp Pro Arg Phe Gly Ala Tyr Val Ala Cys Ala Leu Leu Val Phe Cys
                670                 675                 680 ttc atc tgc ttc atc cag ctt ctc atc ttc cca cac tcc acc ctg atg       2235
Phe Ile Cys Phe Ile Gln Leu Leu Ile Phe Pro His Ser Thr Leu Met
            685                 690                 695 ctt ggg atc tat gcc agc atc ttc ctg ctg cta atc acc gtg ctg           2283
Leu Gly Ile Tyr Ala Ser Ile Phe Leu Leu Leu Ile Thr Val Leu
        700                 705                 710 atc tgt gct gtg tac tcc tgt ggt tct ctg ttc cct aag gcc ctg caa       2331
Ile Cys Ala Val Tyr Ser Cys Gly Ser Leu Phe Pro Lys Ala Leu Gln
    715                 720                 725 cgt ctg tcc cgc agc att gtc cgc tca cgg gca cat agc acc gca gtt       2379
Arg Leu Ser Arg Ser Ile Val Arg Ser Arg Ala His Ser Thr Ala Val
730                 735                 740                 745 ggc atc ttt tcc gtc ctg ctt gtg ttt act tct gcc att gcc aac atg       2427
Gly Ile Phe Ser Val Leu Leu Val Phe Thr Ser Ala Ile Ala Asn Met
                750                 755                 760 ttc acc tgt aac cac acc ccc ata cgg agc tgt gca gcc cgg atg ctg       2475
Phe Thr Cys Asn His Thr Pro Ile Arg Ser Cys Ala Ala Arg Met Leu
            765                 770                 775 aat tta aca cct gct gac atc act gcc tgc cac ctg cag cag ctc aat       2523
Asn Leu Thr Pro Ala Asp Ile Thr Ala Cys His Leu Gln Gln Leu Asn
        780                 785                 790 tac tct ctg ggc ctg gat gct ccc ctg tgt gag ggc acc atg ccc acc       2571
Tyr Ser Leu Gly Leu Asp Ala Pro Leu Cys Glu Gly Thr Met Pro Thr
    795                 800                 805 tgc agc ttt cct gag tac ttc atc ggg aac atg ctg ctg agt ctc ttg       2619
Cys Ser Phe Pro Glu Tyr Phe Ile Gly Asn Met Leu Leu Ser Leu Leu
810                 815                 820                 825
```

```
gcc agc tct gtc ttc ctg cac atc agc agc atc ggg aag ttg gcc atg     2667
Ala Ser Ser Val Phe Leu His Ile Ser Ser Ile Gly Lys Leu Ala Met
            830                 835                 840 atc ttt gtc ttg ggg ctc atc tat ttg gtg ctg ctt ctg ctg ggt ccc     2715
Ile Phe Val Leu Gly Leu Ile Tyr Leu Val Leu Leu Leu Leu Gly Pro
            845                 850                 855 cca gcc acc atc ttt gac aac tat gac cta ctg ctt ggc gtc cat ggc     2763
Pro Ala Thr Ile Phe Asp Asn Tyr Asp Leu Leu Leu Gly Val His Gly
            860                 865                 870 ttg gct tct tcc aat gag acc ttt gat ggg ctg gac tgt cca gct gca     2811
Leu Ala Ser Ser Asn Glu Thr Phe Asp Gly Leu Asp Cys Pro Ala Ala
        875                 880                 885 ggg agg gtg gcc ctc aaa tat atg acc cct gtg att ctg ctg gtg ttt     2859
Gly Arg Val Ala Leu Lys Tyr Met Thr Pro Val Ile Leu Leu Val Phe
890                 895                 900                 905 gcg ctg gcg ctg tat ctg cat gct cag cag gtg gag tcg act gcc cgc     2907
Ala Leu Ala Leu Tyr Leu His Ala Gln Gln Val Glu Ser Thr Ala Arg
                910                 915                 920 cta gac ttc ctc tgg aaa cta cag gca aca ggg gag aag gag gag atg     2955
Leu Asp Phe Leu Trp Lys Leu Gln Ala Thr Gly Glu Lys Glu Glu Met
            925                 930                 935 gag gag cta cag gca tac aac cgg agg ctg ctg cat aac att ctg ccc     3003
Glu Glu Leu Gln Ala Tyr Asn Arg Arg Leu Leu His Asn Ile Leu Pro
        940                 945                 950 aag gac gtg gcg gcc cac ttc ctg gcc cgg gag cgc cgc aat gat gaa     3051
Lys Asp Val Ala Ala His Phe Leu Ala Arg Glu Arg Arg Asn Asp Glu
        955                 960                 965 ctc tac tat cag tcg tgt gag tgt gtg gct gtt atg ttt gcc tcc att     3099
Leu Tyr Tyr Gln Ser Cys Glu Cys Val Ala Val Met Phe Ala Ser Ile
970                 975                 980                 985 gcc aac ttc tct gag ttc tat gtg gag ctg gag gca aac aat gag ggt     3147
Ala Asn Phe Ser Glu Phe Tyr Val Glu Leu Glu Ala Asn Asn Glu Gly
                990                 995                 1000 gtc gag tgc ctg cgg ctg ctc aac gag atc atc gct gac ttt gat gag     3195
Val Glu Cys Leu Arg Leu Leu Asn Glu Ile Ile Ala Asp Phe Asp Glu
            1005                1010                1015 att atc agc gag gag cgg ttc cgg cag ctg gaa aag atc aag acg att     3243
Ile Ile Ser Glu Glu Arg Phe Arg Gln Leu Glu Lys Ile Lys Thr Ile
        1020                1025                1030 ggt agc acc tac atg gct gcc tca ggg ctg aac gcc agc acc tac gat     3291
Gly Ser Thr Tyr Met Ala Ala Ser Gly Leu Asn Ala Ser Thr Tyr Asp
    1035                1040                1045 cag gtg ggc cgc tcc cac atc act gcc ctg gct gac tac gcc atg cgg     3339
Gln Val Gly Arg Ser His Ile Thr Ala Leu Ala Asp Tyr Ala Met Arg
1050                1055                1060                1065 ctc atg gag cag atg aag cac atc aat gag cac tcc ttc aac aat ttc     3387
Leu Met Glu Gln Met Lys His Ile Asn Glu His Ser Phe Asn Asn Phe
            1070                1075                1080 cag atg aag att ggg ctg aac atg ggc cca gtc gtg gca ggt gtc atc     3435
Gln Met Lys Ile Gly Leu Asn Met Gly Pro Val Val Ala Gly Val Ile
        1085                1090                1095 ggg gct cgg aag cca cag tat gac atc tgg ggg aac aca gtg aat gtc     3483
Gly Ala Arg Lys Pro Gln Tyr Asp Ile Trp Gly Asn Thr Val Asn Val
    1100                1105                1110 tct agt cgt atg gac agc acg ggg gtc ccc gac cga atc cag gtg acc     3531
Ser Ser Arg Met Asp Ser Thr Gly Val Pro Asp Arg Ile Gln Val Thr
1115                1120                1125 acg gac ctg tac cag gtt cta gct gcc aag ggc tac cag ctg gag tgt     3579
Thr Asp Leu Tyr Gln Val Leu Ala Ala Lys Gly Tyr Gln Leu Glu Cys
```

-continued

| | | | |
|---|---|---|---|
| 1130 | 1135 | 1140 | 1145 | cga ggg gtg gtc aag gtg aag ggc aag ggg gag atg acc acc tac ttc  3627
Arg Gly Val Val Lys Val Lys Gly Lys Gly Glu Met Thr Thr Tyr Phe
                    1150                1155                1160 ctc aat ggg ggc ccc agc agt taacagggcc cagccacaaa ttcagctgaa  3678
Leu Asn Gly Gly Pro Ser Ser
            1165 gggaccaagg tgggcattga gtggactctg tgctcactgg gtggagctgt ggcagggggc  3738
actgagcctc cagaccctgc taaccacaaa agggaacatc ccagcaggct gtgcttggat  3798
catgctcgtc tgccctcaag ctggaaaaca aggggctacc taccgagagg attatgcaag  3858
tgactttctt tcttacttgg ggtagggctg ttccctctcc aatcttccag cctttgggag  3918
caggggaggg gtcagtagca gaagcagagg gaggcctctt gcctgaggga ttaaaatggc  3978
agcttgccat gcctacccett ccctgtctgt ctgggcagca ggttcagggc tgagcccttc  4038
tttttccctct tttttcctgg gaatattttg tacaatattt tgtacaaaga caggcatgag  4098
gagtgcctat tccatgcttg cctttgcaat acctgcatcc ccagcactgg tcctgggcac  4158
ttcccccaccc cagccaggtg tccctcctat gcacagagca gaggagggag aagctctggg  4218
gagccagctt tggccatatt tcaggagaat gtttccatgt gccaaatctt agtcccatga  4278
tctgtcccca aggggaaca aagggacctc tgacagctta gatttagccc cagttcctgc  4338
acgctccagg gaacggggtg tctggcctca ctggtactgt gaaaaatgct cagagagcaa  4398
gcctgtgtgt ggggatgtca ggtcaggagc tggaagttca cctgcaggtg ccaaagagca  4458
ggccggccag ggctggggca gtgccagact ctgatctgag accccgtcg gggtccagat  4518
caggtcactc tgccccagtg ctctcttgct gtctgctgac aagggggcat ggagcatctc  4578
ttcctcttct gttgccaaat agaaaagggt cagggcatgg agaaaggtga ccctgatccc  4638
aaacctgccc tcccaagtct ctggtgttgg ggagggcccg tgtgtttgtg taactgtgtg  4698
tgcatgttgg tctttgtgtg catatctgtt ttccaggtct atgtgagtcc ttgtgctcct  4758
gctcctcagc tctccacccc aggttgcctc tctcctgtgg gcctctgtct tctgggaata  4818
aagcagggtt tcctacttca ggggatgtag agagatgccc aggttgcaca ggagtgggat  4878
ggggtgtggt agcaaaagga gggagaggag tccttttgt gccaaatccc taagtgccgt  4938
tcgg  4942

<210> SEQ ID NO 2
<211> LENGTH: 1168
<212> TYPE: PRT
<213> ORGANISM: human type VI adenylyl cyclase

<400> SEQUENCE: 2

Met Ser Trp Phe Ser Gly Leu Leu Val Pro Lys Val Asp Glu Arg Lys
1               5                   10                  15

Thr Ala Trp Gly Glu Arg Asn Gly Gln Lys Arg Ser Arg Arg Arg Gly
            20                  25                  30

Thr Arg Ala Gly Gly Phe Cys Thr Pro Arg Tyr Met Ser Cys Leu Arg
        35                  40                  45

Asp Ala Glu Pro Pro Ser Pro Thr Pro Ala Gly Pro Pro Arg Cys Pro
    50                  55                  60

Trp Gln Asp Asp Ala Phe Ile Arg Arg Gly Gly Pro Gly Lys Gly Lys
65                  70                  75                  80

Glu Leu Gly Leu Arg Ala Val Ala Leu Gly Phe Glu Asp Thr Glu Val
                85                  90                  95

```
Thr Thr Thr Ala Gly Gly Thr Ala Glu Val Ala Pro Asp Ala Val Pro
            100                 105                 110

Arg Ser Gly Arg Ser Cys Trp Arg Arg Leu Val Gln Val Phe Gln Ser
            115                 120                 125

Lys Gln Phe Arg Ser Ala Lys Leu Glu His Leu Tyr Gln Arg Tyr Phe
            130                 135                 140

Phe Gln Met Asn Gln Ser Ser Leu Thr Leu Leu Met Ala Val Leu Val
145                 150                 155                 160

Leu Leu Thr Ala Val Leu Leu Ala Phe His Ala Ala Pro Ala Arg Pro
            165                 170                 175

Gln Pro Ala Tyr Val Ala Leu Leu Ala Cys Ala Ala Ala Leu Phe Val
            180                 185                 190

Gly Leu Met Val Val Cys Asn Arg His Ser Phe Arg Gln Asp Ser Met
            195                 200                 205

Trp Val Val Ser Tyr Val Val Leu Gly Ile Leu Ala Ala Val Gln Val
            210                 215                 220

Gly Gly Ala Leu Ala Ala Asp Pro Arg Ser Pro Ser Ala Gly Leu Trp
225                 230                 235                 240

Cys Pro Val Phe Phe Val Tyr Ile Ala Tyr Thr Leu Leu Pro Ile Arg
            245                 250                 255

Met Arg Ala Ala Val Leu Ser Gly Leu Gly Leu Ser Thr Leu His Leu
            260                 265                 270

Ile Leu Ala Trp Gln Leu Asn Arg Gly Asp Ala Phe Leu Trp Lys Gln
            275                 280                 285

Leu Gly Ala Asn Val Leu Leu Phe Leu Cys Thr Asn Val Ile Gly Ile
            290                 295                 300

Cys Thr His Tyr Pro Ala Glu Val Ser Gln Arg Gln Ala Phe Gln Glu
305                 310                 315                 320

Thr Arg Gly Tyr Ile Gln Ala Arg Leu His Leu Gln His Glu Asn Arg
            325                 330                 335

Gln Gln Glu Arg Leu Leu Leu Ser Val Leu Pro Gln His Val Ala Met
            340                 345                 350

Glu Met Lys Glu Asp Ile Asn Thr Lys Lys Glu Asp Met Met Phe His
            355                 360                 365

Lys Ile Tyr Ile Gln Lys His Asp Asn Val Ser Ile Leu Phe Ala Asp
            370                 375                 380

Ile Glu Gly Phe Thr Ser Leu Ala Ser Gln Cys Thr Ala Gln Glu Leu
385                 390                 395                 400

Val Met Thr Leu Asn Glu Leu Phe Ala Arg Phe Asp Lys Leu Ala Ala
            405                 410                 415

Glu Asn His Cys Leu Arg Ile Lys Ile Leu Gly Asp Cys Tyr Tyr Cys
            420                 425                 430

Val Ser Gly Leu Pro Glu Ala Arg Ala Asp His Ala His Cys Cys Val
            435                 440                 445

Glu Met Gly Val Asp Met Ile Glu Ala Ile Ser Leu Val Arg Glu Val
            450                 455                 460

Thr Gly Val Asn Val Asn Met Arg Val Gly Ile His Ser Gly Arg Val
465                 470                 475                 480

His Cys Gly Val Leu Gly Leu Arg Lys Trp Gln Phe Asp Val Trp Ser
            485                 490                 495

Asn Asp Val Thr Leu Ala Asn His Met Glu Ala Gly Gly Arg Ala Gly
            500                 505                 510
```

```
Arg Ile His Ile Thr Arg Ala Thr Leu Gln Tyr Leu Asn Gly Asp Tyr
        515                 520                 525

Glu Val Glu Pro Gly Arg Gly Gly Glu Arg Asn Ala Tyr Leu Lys Glu
        530                 535                 540

Gln His Ile Glu Thr Phe Leu Ile Leu Gly Ala Ser Gln Lys Arg Lys
545                 550                 555                 560

Glu Glu Lys Ala Met Leu Ala Lys Leu Gln Arg Thr Arg Ala Asn Ser
                565                 570                 575

Met Glu Gly Leu Met Pro Arg Trp Val Pro Asp Arg Ala Phe Ser Arg
            580                 585                 590

Thr Lys Asp Ser Lys Ala Phe Arg Gln Met Gly Ile Asp Asp Ser Ser
        595                 600                 605

Lys Asp Asn Arg Gly Thr Gln Asp Ala Leu Asn Pro Glu Asp Glu Val
        610                 615                 620

Asp Glu Phe Leu Ser Arg Ala Ile Asp Ala Arg Ser Ile Asp Gln Leu
625                 630                 635                 640

Arg Lys Asp His Val Arg Arg Phe Leu Leu Thr Phe Gln Arg Glu Asp
                645                 650                 655

Leu Glu Lys Lys Tyr Ser Arg Lys Val Asp Pro Arg Phe Gly Ala Tyr
            660                 665                 670

Val Ala Cys Ala Leu Leu Val Phe Cys Phe Ile Cys Phe Ile Gln Leu
        675                 680                 685

Leu Ile Phe Pro His Ser Thr Leu Met Leu Gly Ile Tyr Ala Ser Ile
        690                 695                 700

Phe Leu Leu Leu Leu Ile Thr Val Leu Ile Cys Ala Val Tyr Ser Cys
705                 710                 715                 720

Gly Ser Leu Phe Pro Lys Ala Leu Gln Arg Leu Ser Arg Ser Ile Val
            725                 730                 735

Arg Ser Arg Ala His Ser Thr Ala Val Gly Ile Phe Ser Val Leu Leu
            740                 745                 750

Val Phe Thr Ser Ala Ile Ala Asn Met Phe Thr Cys Asn His Thr Pro
        755                 760                 765

Ile Arg Ser Cys Ala Ala Arg Met Leu Asn Leu Thr Pro Ala Asp Ile
        770                 775                 780

Thr Ala Cys His Leu Gln Gln Leu Asn Tyr Ser Leu Gly Leu Asp Ala
785                 790                 795                 800

Pro Leu Cys Glu Gly Thr Met Pro Thr Cys Ser Phe Pro Glu Tyr Phe
                805                 810                 815

Ile Gly Asn Met Leu Leu Ser Leu Leu Ala Ser Ser Val Phe Leu His
            820                 825                 830

Ile Ser Ser Ile Gly Lys Leu Ala Met Ile Phe Val Leu Gly Leu Ile
        835                 840                 845

Tyr Leu Val Leu Leu Leu Gly Pro Pro Ala Thr Ile Phe Asp Asn
        850                 855                 860

Tyr Asp Leu Leu Leu Gly Val His Gly Leu Ala Ser Ser Asn Glu Thr
865                 870                 875                 880

Phe Asp Gly Leu Asp Cys Pro Ala Ala Gly Arg Val Ala Leu Lys Tyr
                885                 890                 895

Met Thr Pro Val Ile Leu Leu Val Phe Ala Leu Ala Leu Tyr Leu His
            900                 905                 910

Ala Gln Gln Val Glu Ser Thr Ala Arg Leu Asp Phe Leu Trp Lys Leu
        915                 920                 925

Gln Ala Thr Gly Glu Lys Glu Glu Met Glu Glu Leu Gln Ala Tyr Asn
```

-continued

```
            930                 935                 940
Arg Arg Leu Leu His Asn Ile Leu Pro Lys Asp Val Ala Ala His Phe
945                 950                 955                 960

Leu Ala Arg Glu Arg Arg Asn Asp Glu Leu Tyr Tyr Gln Ser Cys Glu
                965                 970                 975

Cys Val Ala Val Met Phe Ala Ser Ile Ala Asn Phe Ser Glu Phe Tyr
                980                 985                 990

Val Glu Leu Glu Ala Asn Asn Glu Gly Val Glu Cys Leu Arg Leu Leu
                995                1000                1005

Asn Glu Ile Ile Ala Asp Phe Asp Glu Ile Ile Ser Glu Glu Arg Phe
   1010                1015                1020

Arg Gln Leu Glu Lys Ile Lys Thr Ile Gly Ser Thr Tyr Met Ala Ala
1025                1030                1035                1040

Ser Gly Leu Asn Ala Ser Thr Tyr Asp Gln Val Gly Arg Ser His Ile
                1045                1050                1055

Thr Ala Leu Ala Asp Tyr Ala Met Arg Leu Met Glu Gln Met Lys His
                1060                1065                1070

Ile Asn Glu His Ser Phe Asn Asn Phe Gln Met Lys Ile Gly Leu Asn
       1075                1080                1085

Met Gly Pro Val Val Ala Gly Val Ile Gly Ala Arg Lys Pro Gln Tyr
   1090                1095                1100

Asp Ile Trp Gly Asn Thr Val Asn Val Ser Ser Arg Met Asp Ser Thr
1105                1110                1115                1120

Gly Val Pro Asp Arg Ile Gln Val Thr Thr Asp Leu Tyr Gln Val Leu
                1125                1130                1135

Ala Ala Lys Gly Tyr Gln Leu Glu Cys Arg Gly Val Val Lys Val Lys
            1140                1145                1150

Gly Lys Gly Glu Met Thr Thr Tyr Phe Leu Asn Gly Gly Pro Ser Ser
            1155                1160                1165
```